(12) United States Patent
Rosenfeld et al.

(10) Patent No.: US 7,191,068 B2
(45) Date of Patent: Mar. 13, 2007

(54) PROTEOMIC ANALYSIS OF BIOLOGICAL FLUIDS

(75) Inventors: Ron Rosenfeld, Los Altos, CA (US); Sri Nagalla, Hillsboro, OR (US); Mike Gravett, Portland, OR (US)

(73) Assignee: Proteogenix, Inc., Portland, OR (US)

( * ) Notice: Subject to any disclaimer, the term of this patent is extended or adjusted under 35 U.S.C. 154(b) by 208 days.

(21) Appl. No.: 10/400,005

(22) Filed: Mar. 25, 2003

(65) Prior Publication Data

US 2004/0197930 A1    Oct. 7, 2004

(51) Int. Cl.
G01N 33/48    (2006.01)
G01N 31/00    (2006.01)

(52) U.S. Cl. .............................. 702/19; 702/20; 702/23

(58) Field of Classification Search ................ 435/7.92; 530/300, 350; 702/19, 20
See application file for complete search history.

(56) References Cited

U.S. PATENT DOCUMENTS 6,406,921 B1    6/2002 Wagner et al.
2004/0241775 A1*  12/2004 Romero et al. ............ 435/7.92

FOREIGN PATENT DOCUMENTS

WO    WO2004/043238    5/2004
WO    WO2004/045379    6/2004

OTHER PUBLICATIONS

Vadillo-Ortega et al., Am. J. Obstet. Gynecol., vol. 186, pp. 128-138, Jan. 2002.*
Agerberth, B., et al., "FALL-39, a putative human peptide antibiotic, is cysteine-free and expressed in bone marrow and testis", *Proc. Natl. Acad. Sci.*, USA 3;92(1):195-199, 1995.
Arai, M., et al., "Differential Developmentally Regulated Expression of Gelsolin Family Members in the Mouse", *Dev. Dyn.*, 215, 297-307, 1999.
Ball, et al., "An integrated approach utilizing artifical neural networks and SELDI mass spectrometry for the classification of human tumors and rapid identification of potential biomarkers", *Bioinformatics* 18(3):395-404, 2002.
Bejar, R., et al., "Antenatal origin of neurologic damage in newborn infants, I. Preterm Infants", *Am. J. Obstet. Gynecol.* 159(2):357-363, Aug. 1988.
Courchesna and Patterson, "Identification of Proteins by Matrix-Assisted Laser Desorption/Ionization Mass Spectrometry Using Peptide and Fragment Ion Masses", *Methods Mol. Biol.* 112(2-D):487-511, 1999.

Creasy, R.K., et al., "Preterm Labor and Delivery", In *Maternal-Fetal Medicine*, Creasy, R.K., Resnik, R., (eds.), W. B. Saunders Company, Philadelphia, PA, 4th edition, Chapter 32, pp. 498-531, 1999.
Cuckle, H., "Biochemical screening for Down syndrome", *Eur. J. Obstet Gynecol Reprod. Biol.*, 92(1):97-101, 2000.
Dabiri, G.S., "Molecular Cloning of Human Macrophage Capping Protein cDNA. A Unique Member of the Gelsolin/Villin Family Expressed Primarily in Macrophages", *J. Biol. Chem.*, 267(23):16545-16552, 1992.
Ducsay, C.A., et al., "Simplified Vest and Tether System for Maintenance of Chronically Catheterized Pregnant Rhesus Monkeys", *Lab. Anim. Sci.*, 38(3):343-344, Jun. 1988.
Duff, P., et al., "The course of labor in term patients with chorioamnionitis", *American Journal of Obstetrics and Gynecology*, 147(4):391-395, Oct. 1983.
Gibbs, R.S., et al., "Management of acute chorioamnionitis", *American Journal of Obstetrics and Gynecology*, 136(6):709-713, Mar. 1980.
Gilstrap III, L.C., et al., "Intrapartum treatment of acute chorioamnionitis: Impact on neonatal sepsis", *Am. J. Obstet. Gynecol.* 159(3):579-583, Sep. 1988.
Goetz, D.H., et al., "The Neutrophil Lipocalin NGAL Is a Bacteriostatic Agent that Interferes with Siderophore-Mediated Iron Acquisition", *Mol. Cell*, 10(5):1033-1043, 2002.
Gravett, et al., "An experimental model for intraamniotic infection and preterm labor in rhesus monkeys", *Am. J. Obstet. Gynecol.*, 171(6):1660-7, Dec. 1994.
Grether, J.K., et al., "Maternal Infection and Cerebral Palsy in Infants of Normal Birth Weight", *JAMA* 278(3):207-211, Jul. 1997.
Gursoy, T., et al., "Preeclampsia Disrupts the Normal Physiology of Leptin", *Am. J. Perinatol*, 19(6):303-310, 2002.

(Continued)

Primary Examiner—John S. Brusca
Assistant Examiner—Shubo(Joe) Zhou
(74) *Attorney, Agent, or Firm*—Ginger R. Dreger; Steven P. Lendaris; Heller Ehrman LLP

(57) ABSTRACT

The invention concerns the identification of proteomes of biological fluids and their use in determining the state of maternal/fetal conditions, including maternal conditions of fetal origin, chromosomal aneuploidies, and fetal diseases associated with fetal growth and maturation. In particular, the invention concerns the identification of the proteome of amniotic fluid (multiple proteins representing the composition of amniotic fluid) and the correlation of characteristic changes in the normal proteome with various pathologic maternal/fetal conditions, such as intra-amniotic infection, or chromosomal defects.

44 Claims, 16 Drawing Sheets

OTHER PUBLICATIONS

Haluska, G.J., et al., "Temporal changes in uterine activity and prostaglandin response to RU486 in *Rhesus macaques* in late gestation", *Am. J. Obstet. Gynecol*, 157:1487-1495, 1987.

Hitti, J., et al., "Amniotic fluid tumor necrosis factor-α and the risk of respiratory distress syndrome among preterm infants", *AM. J. Obstet. Gynecol*. 177:50-56, 1997.

Hook, E. B., et al., "The Frequency of Chromosome Abnormalities Detected in Consecutive Newborn Studies-Differences Between Studies-Results by Sex and by Severity of Phenotypic Involvement", In Hook, E.B., Proter, I.H. (eds.), *Population Cytogenetics*, pp. 63-79, New York, Academic Press, 1978.

Issaq, J.H., et al., "The SELDI-TOF MS Approach to Proteomins: Protein Profiling and Biomarker Identification", *Biochem. Biophys. Res. Commun.*, 5:292(3):587-92, 2000.

Jensen, O.N., et al., "Direct observation of UV-crosslinked Protein-Nucleic Acid Complexes by Matrix-assisted Laser Desorption Oonization Mass Spectrometry", *Rapid Commun. Mass. Spectrom.*, 7:496-501, 1993.

Li, et al., "Proteomics and Bioinformatics Approaches for Identification of Serum Biomarkers to Detect Breast Cancer", *Clinical Chemsitry Journal*, 48(8):1296-1304, 2002.

Lomas, D.A., et al., "Serpinopathies and the Conformational Dementias", *Nat. Rev. Genet* 3:759-768, 2002.

Lopez-Zeno, J.A., et al., "A Controlled Trial of a Program for the Active Management of Labor", *N. Engl. J. Med*. 326(7):450-454, Feb. 1992.

Marvin, L., et al., "Identification of proteins from one-dimensional sodium dodecyl sulfate-polyacrylamide gel electrophoresis using electrospray quadrupole-time-of-flight tandem mass spectrometry", *Rapid Commun. Mass. Spectrom*. 14:1287-1292, 2000.

Meis, P.J., et al.., "Factor associated with preterm birth in Cardiff, Wales: II. Indicated and spontaneous preterm birth", *Am. J. Obstet. Gynecol*., 173(2):597-602, Aug. 1995.

Morales, W.J., "The Effect of Chorioamnionitis on the Developmental Outcome of Preterm Infants at One year", *Obstetrics and Gynecology*, 70(2):183-186, Aug. 1987.

Newton, E.R., "Chorioamnionitis and Intraamniotic Infection", *Clin. Obstet. Gynecol.*, 36(4):795-808, Dec. 1993.

Newton, E.R., et al., "Logistic Regression Analysis of Risk Factors for Intra-Amniotic Infection", *Obstet. Gynecol.*, 73(4):571-575, Apr. 1989.

Ohlsson, A., et al., "An analysis of antenatal tests to detect infection at preterm premature rupture of the membranes", *American Journal of Obstetrics and Gynecology*, 162(3):809-818, Mar. 1990.

Pereira, H.A., "CAP37, a neutrophil-derived multifunctional inflammatory mediator", *J. Leukoc Biol*. 57:805-812, 1995.

Petricoin, III, E.F., et al., "Use of poteomic patterns in serum to identify ovarian cancer", *The Lancet* 359:572-77, Feb. 2002.

Romero, R., et al., "The Role of Systemic and Intrauterine Infection in Preterm Parturition", *Annuals of the New York Academy of Science* 622:355-375, May 1991.

Schweitzer, B., et al., "Measuring proteins on microarrays", *Curr. Opin. Biotechnol*., 13:14-9, 2002.

Soper, D.E., et al., "Risk factors for intraamniotic infection: A prospective epidemicologic study", *American Journal of Obstetrics and Gynecology* 161(3):562-568, Sep. 1989.

Speck, O., et al., "Moesin functions antagonistically to the Rho pathway to maintain epithelial integrity", *Nature* 421(2):83-87, 2003.

Tabb, D.L., et al., "DTASelect and Contrast: Tools for Assembling and Comparing Protein Identifications from Shotgun Proteomics", *J. Proteome Res*. 1:21-26, 2002.

Tang, B.L., "Inhibitors of neuronal regeneration: mediators and signaling mechanisms", *Neurochem. Int*., 42(3):189-203, 2003.

Taylor, J.A., et al., "Implementation and Uses of Automated de Novo Peptide Sequencing by Tandem Mass Spectrometry", *Anal. Chem*. 73(11):2594-604, 2001.

Thorey, I.S., et al., "The $Ca^{2+}$-binding Proteins S100A8 and S100A9 Are Encoded by Novel Injury-regulated Genes", *J. Biol. Chem*. 276(38):35818-35825, 2001.

Vray, B., et al., "Immunomodulatory properties of cystatins", *Cell Mol. Life Sci.*, 59:1503-1512, 2002.

Watts, D.H., et al., "The Association of Occult Amniotic Fuid Infection with Gestational Age and Neonatal Outcome Among Women in Preterm Labor", *Obstet. Gynecol*. 79(3):351-357, Mar. 1992.

Weitzdoerfer, R., et al., "Reduction of action-related protein complex 2/3 in fetal Down syndrome brain", *Biochem. Biophys. Res. Commun*. 293:836-841, 2002.

Wilson and Nock, "Recent Developments in Protein Microarray Technology", *Angew Chem. Int. Ed. Engl*. 42(5):494-500, 2003.

Wu, C., et al., "Role of 14-3-3 proteins in early Xenopus development", *Mech. Dev.*, 119, 45-54, 2002.

Yates, et al., Automated Protein Identification Using Microcolumn Liquid Chromatography-Tandem Mass Spectrometry, *Methods Mol. Biol*. 112(2-D):553-569, 1999.

Zhou, H., et al., "Solution and chip arrays in protein profiling", *Trends Biotechnol*. 19(10):S34-S39, 2001.

Zhu, et al., "Protein arrays and microarrays", *Current Opin. Chem. Biol*., 5:40-45, 2001.

Gravett, Michael, et al., "Diagnosis of Intra-amniotic Infection by Proteomic Profiling and Identification of Novel Biomarkers", Journal of American Medical Association, vol. 292, No. 4, pp. 462-469, Jul. 28, 2004.

Greene, Nicholas, et al., "Differential Protein Expression at the Stage of Neural Tube Closure in the Mouse Embryo", The Journal of Biological Chemistry, vol. 277, No. 44, Issue of Nov. 1, pp. 41645-41651, 2002.

Gulesserian, Talin. et al., Aberrant Expression of Centractin and Capping Proteins, Integral Constituents of the Dynactin Complex, in Fetal Down Syndrome Brain, Biochemical and Biophysical Research Communication, vol. 291, No. 1, pp. 62-67, Feb. 15, 2002.

Liberatori, Sabrina, et al., "A two-dimensional protein map of human amniotic fluid at 17 weeks' gestation", Electrophoresis, vol. 18, p. 2816-2822, Dec. 1997.

Pellieux, Corinne, et al., "Cap G, a Gelsolin Family Protein Modulating Protective Effects of Unidirectional Shear Stress", The Journal of Biological Chemistry, vol. 278, No. 31, Issue of Aug. 1, pp. 29136-29144, 2003.

Romero, Roberto, et al., "Proteomic profiling of premature labor: A method to identify clinical biomarkers and mechanisms of disease", American Journal of Obstetrics and Gynecology, vol. 189, No. 6, Supplement, Sep. 2003.

Tashima, Lily, et al., "Genes Unregulated in Human Fetal Membranes by Infection or Labor", Obstetrics and Gynecology, vol. 94, No. 3, Sep. 1999.

Winkler, U., et al., "Urinary Protein Patterns for Early Detection of Preeclampsia", Contributions to Nephrology, vol. 68, pp. 227-229, Karger, Basel 1988.

* cited by examiner

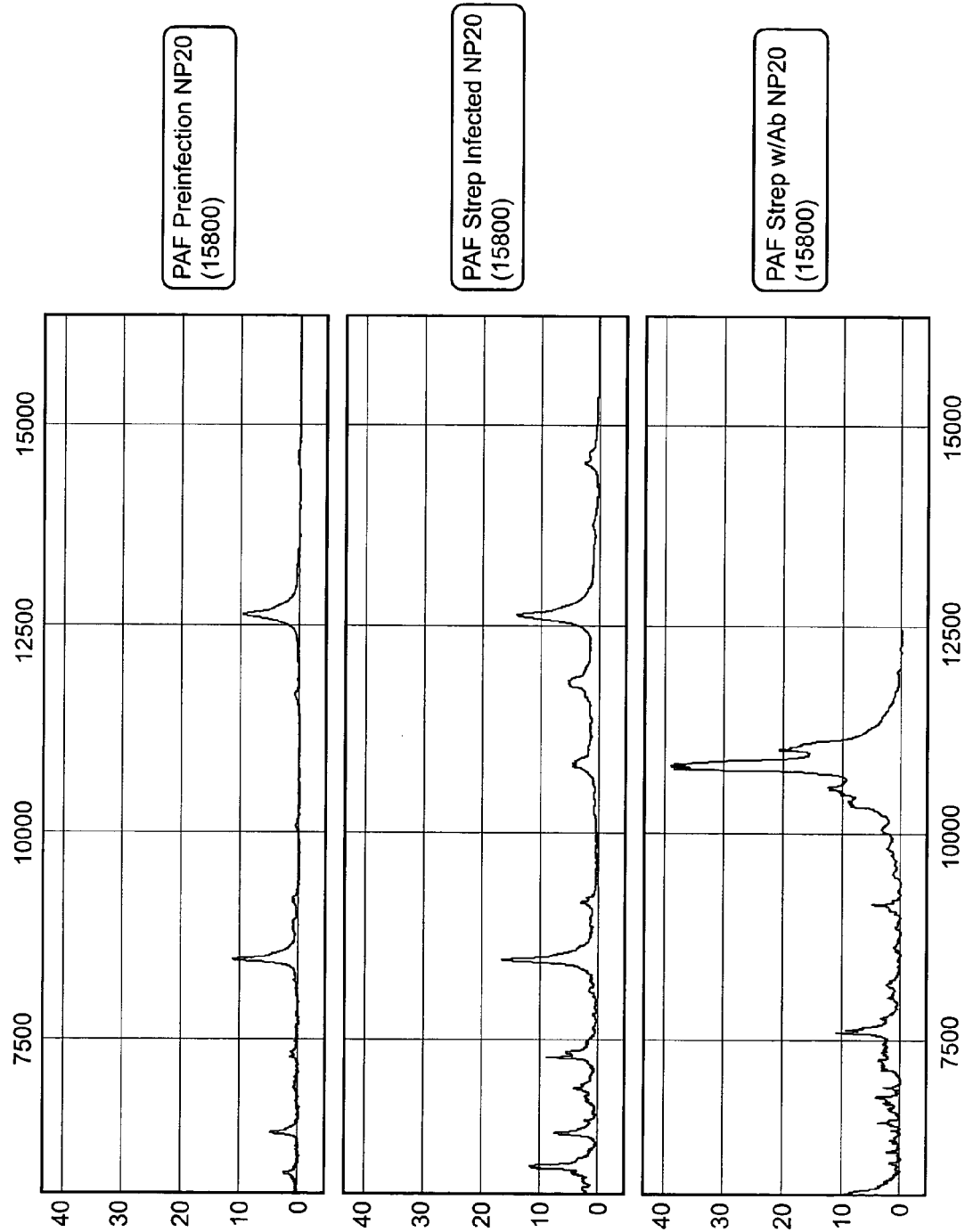

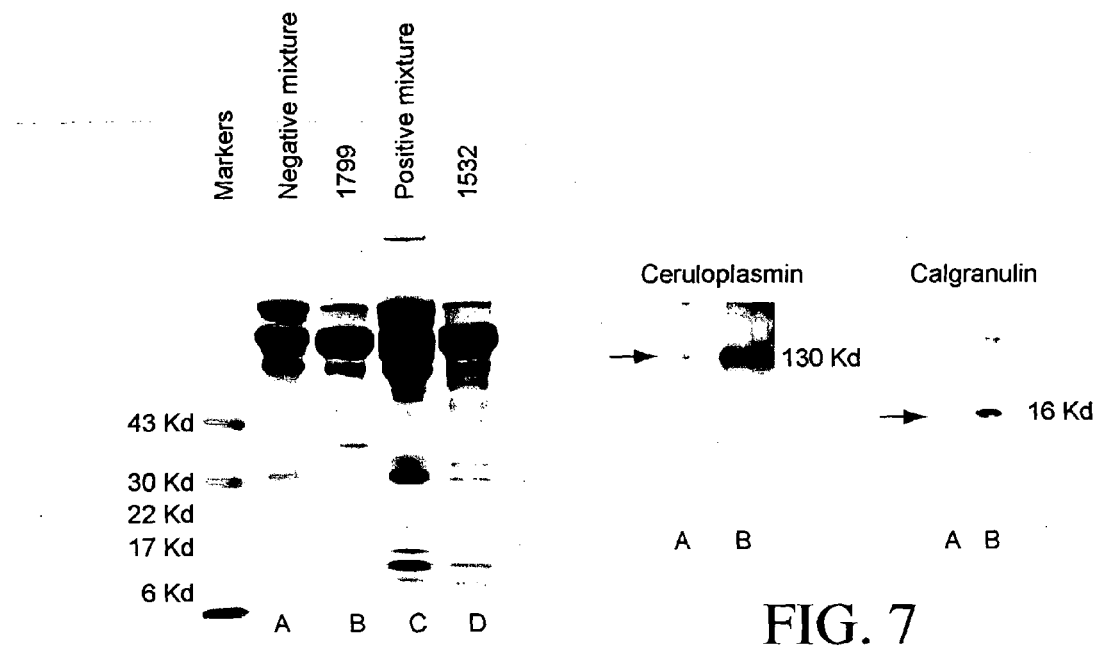
FIG. 5
FIG. 7
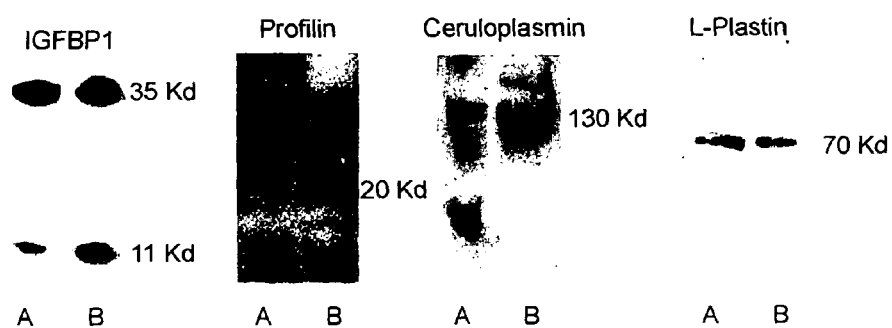
FIG. 6

PRO1_HUMAN (P07737) Profilin I

AGWNAYIDNL MADGTCQDAA IVGYK**DSPSV WAAVPGKTFV
NITPAEVGVL VGK**DRSSFYV NGLTLGGQKC SVIRDSLLQD
GEFSMDLRTK STGGAPTFNV TVTKTDKTLV LLMGKEGVHG
GLINKKCYEM ASHLRRSQY                          (SEQ ID NO: 5)

| | | | | | |
|---|---|---|---|---|---|
| (1) PSVWAAA[GP]R | m/z=607.2974 | z=2 | S=8.4 | N=1 | (SEQ ID NO: 6) |
| (2) STGGAPTFNVTVTK | m/z=691.36 | z=2 | S=9.9 | N=1 | (SEQ ID NO: 7) |
| (3) TFVNITPAEVGVLVGK | m/z=823.46 | z=2 | S=9.8 | N=1 | (SEQ ID NO: 8) |
| (4) DSPSVWAAVPGK | m/z=608.31 | z=2 | S=10.0 | N=1 | (SEQ ID NO: 9) |
| (5) DSPSVWAAVPGK | m/z=608.31 | z=2 | S=10.0 | N=1 | (SEQ ID NO: 10) |
| (6) TFVNITPAEVGVLVGK | m/z=823.46 | z=2 | S=9.8 | N=1 | (SEQ ID NO: 11) |

FIG. 11

MSEVPVARVWLVLLLLTVQVGVTAGAPWQCAPCSAEKLA
LCPPVSASCSEVTRSAGCGCCPMCALPLGAACGVATARC
ARGLSCR*alpgeqqplhaltr*GQGACVQESDASAPHAAEAGSP
ESPESTEITEEELLDNFHLMAPSEEDHSILWDAISTYDGSK
**ALHVTNIKKWKEPCRIELYRVVESLAKAQETSGEEISKFY
LPNCNKNGFYHSRQCETSMDGEAGLCWCVYPWNGK***rip
gspeir*GDPNCQIYFN**VQN                          (SEQ ID NO: 1)

*alpgeqqplhaltr*                               (SEQ ID NO: 2)

*ripgspeir*                                    (SEQ ID NO: 3)

**ALHVTNIKKWKEPCRIELYRVVESLAKAQETSGEEISKFYL
PNCNKNGFYHSRQCETSMDGEAGLCWCVYPWNGK***ripgsp
eir*GDPNCQIYFN                              (SEQ ID NO: 4)

FIG. 12

PROTEOMIC ANALYSIS OF BIOLOGICAL FLUIDS

BACKGROUND OF THE INVENTION

1. Field of the Invention

The invention concerns the identification of proteomes of biological fluids and their use in determining the state of maternal/fetal conditions, including maternal conditions of fetal origin, chromosomal aneuploidies, and fetal diseases associated with fetal growth and maturation. In particular, the invention concerns the identification of the proteome of amniotic fluid (multiple proteins representing the composition of amniotic fluid) and the correlation of characteristic changes in the normal proteome with various pathologic maternal/fetal conditions, such as intra-amniotic infection, or chromosomal defects.

2. Description of the Related Art

Proteomics

The large-scale analysis of protein expression patterns is emerging as an important and necessary complement to current DNA cloning and gene profiling approaches (Pandey and Mann, *Nature* 405:837–46 (2000)). DNA sequence information is helpful in deducing some structural and potential protein modifications based on homology methods, but it does not provide information on regulation of protein function through post-translational modifications, proteolysis or compartmentalization.

Traditional gel-based methods, such as one- and two-dimensional gel electrophoresis are useful for small-scale protein detection (<1,000 proteins), but these require large sample quantity (Lilley K S, Razzaq A, Dupree P: Two-dimensional gel electrophoresis: recent advances in sample preparation, detection and quantitation. Curr Opin Chem Biol. 6(1):46–50, 2002). Approaches to overcome this limitation include matrix-assisted or surface-enhanced laser desorption/ionization (MALDI or SELDI) time-of-flight mass spectrometers that accurately generate profiles showing the masses of proteins in a sample. These patterns or profiles can be used to identify and monitor various diseases. The second level of identification comes from coupling peptide mapping to tandem mass spectrometry to generate amino acid sequence information from peptide fragments. This can, for example, be achieved by coupling the MALDI/SELDI or ESI to quadrupole time-of-flight MS (Qq-TOF MS). The latter method can also be used for quantification of specific peptides (ICAT technology).

Diagnosis of Pathologic Maternal/Fetal Conditions

There are numerous pathologic maternal and fetal conditions, such as intra-amniotic infection (IAI), preeclampsia, preterm delivery and labor, and chromosomal aneuploidies, that may develop during pregnancy and compromise the well-being or, in some instances, threaten the life of the mother and/or the fetus or newborn. Early diagnosis of such conditions is critical to allow timely treatment and intervention. Unfortunately, early diagnosis for most of these conditions is difficult because the clinical signs and symptoms occur late, and are often non-specific and inconsistent. For example, the clinical symptoms of IAI typically include maternal fever and leukocytosis, but these symptoms often occur later and are neither sensitive nor specific. Thus, Gravett et al., *Am. J. Obstet. Gynecol.* 171:1660–7 (1994), utilizing a non-human primate model, demonstrated that following experimental intra-amniotic infection with Group B streptococcus, fever and leukocytosis are present only 50% of the time at the onset of infection-induced preterm labor, which occurs 28 to 40 hours after experimental infection. Therefore, to avoid a delay in diagnosis, a high index of suspicion and the appropriate use of adjunctive laboratory tests, are warranted. The clinical criteria commonly used to diagnose IAI include maternal fever ($\geq 37.8°$ C.), along with two or more of the following: maternal leukocytosis ($\geq 15,000/mm^3$), maternal or fetal tachycardia, uterine tenderness, or foul-smelling amniotic fluid.

Because of the inconsistency of clinical features, other adjunctive laboratory tests have been utilized to aid in the diagnosis of IAI. These include: measurement of maternal C-reactive protein, direct examination of amniotic fluid for leukocytes or bacteria on Gram stain, amniotic fluid culture, measurement of amniotic fluid glucose concentrations, detection of amniotic fluid leukocyte esterase, detection of bacterial organic acids by gas-liquid chromatography, measurements of various amniotic fluid or vaginal cytokines (e.g., interleukins 2, 4, 6, granulocyte colony-stimulating factor, and tumor necrosis factor-$\alpha$), matrix metalloproteinase-9, lactoferrin, and assessment of fetal activity (biophysical profile) by ultrasonography. Measurement of cytokines or other biochemical factors is expensive, generally not clinically available, and is primarily a research tool. Further, the testing efficiency of these tests has not been consistently better than more readily available traditional tests such as amniotic fluid Gram stain and culture, amniotic fluid glucose concentrations, and detection of amniotic fluid leukocyte esterase. The efficiency of these tests has been previously extensively reviewed. (Ohlsson, A. and Wang, E.: An analysis of antenatal tests to detect infection at preterm rupture of the membranes. *American Journal of Obstetrics and Gynecology* 162:809, 1990). Although all have reasonable sensitivity, specificity, and predictive value none are sufficiently sensitive or specific to be utilized independently of clinical features in the diagnosis of IAI.

Accordingly, there is a great need for new approaches that allow early and accurate diagnosis of IAI and other pathologic maternal/fetal conditions.

It is particularly desirable to develop new, efficient and reliable non-invasive methods for the diagnosis of chromosomal aneuploidies. At present the definitive diagnosis of chromosomal aneuploidies following maternal serum screening and ultrasound requires a mid-trimester genetic amniocentesis. This is an invasive procedure associated with a 0.5% risk of loss of the pregnancy. Further, chromosomal analysis of amniotic fluid cells is a labor-intensive and time-consuming procedure, taking up to 2 weeks. Reliable tests are therefore necessary to improve the detection of chromosomal aneuploidies from maternal serum, or other biological fluids, reduce the unacceptably high false positive rate of maternal screening, and increase the speed and efficiency of diagnosis from amniotic fluid following amniocentesis. Other patahologic aneuploidic conditions, such as Klinefelter syndrome and Turner syndrome, may be entirely missed by screening with ultrasonography or conventional maternal serum screening.

SUMMARY OF THE INVENTION

The present invention provides non-invasive and sensitive methods for the early diagnosis, prognosis, and monitoring of pathologic fetal/maternal conditions, by proteomic analysis of biological fluids.

The present invention further provides proteomic profiles of biological fluids, such as amniotic fluid and maternal serum, which enable the diagnosis, prognosis, and monitoring of various pathologic fetal/maternal conditions, including, without limitation, intra-amniotic infection (IAI), chromosomal aneuploidies, and fetal diseases associated with fetal growth and maturation. In particular, the present invention provides normal and pathologic proteomic profiles for IAI and chromosomal aneuploidies. The determination of the normal proteomic profile is of great importance, since it enables the elimination of the fetal/maternal condition in question (negative diagnosis), which eliminates the need to subject the patient to unnecessary and potentially dangerous treatment or intervention.

The present invention further provides specific biomarkers for the presence and state of IAI and chromosomal aneuploidies, which are differentially expressed in biological fluids, such as amniotic fluid or maternal serum, when such pathologic conditions are present.

In one aspect, the invention concerns a method for determining the state of a maternal or fetal condition, comprising comparing the proteomic profile of a test sample of a biological fluid obtained from a mammalian subject with the proteomic profile of a normal sample, or a reference proteomic profile comprising at least one unique expression signature characteristic of such condition.

In an embodiment of this method, the mammalian subject is a pregnant female, preferably primate or human.

In another embodiment, the maternal condition is selected from the group consisting of intrauterine infection, preeclampsia, and preterm labor.

In a further embodiment, the fetal condition is selected from the group consisting of chromosomal aneuploidies, congenital malformation, gestational age and fetal maturity, where the chromosomal aneuploidy can, for example, be Down_syndrome, trisomy-13, trisomy-18, Turner syndrome, or Klinefelter syndrome.

Any biological fluid can be used in performing the method of the invention, including, without limitation, amniotic fluid, serum, plasma, urine, cerebrospinal fluid, breast milk, mucus, and saliva, preferably, amniotic fluid or maternal serum.

In a further embodiment, the proteomic profile of the test sample comprises information of at least 2 proteins, or at least 5 proteins, or at least 10 proteins, or at least 20 proteins, or at least 50 proteins.

In a specific embodiment, the proteomic profile is a mass spectrum.

In another embodiment, the mass spectrum comprises at least one unique expression signature in the 3 to 5 kDa range of the mass spectrum.

In yet another embodiment, the mass spectrum comprises at least one unique expression signature in the 10 to 12 kDa range of the mass spectrum.

In a further embodiment, the maternal condition is intra-amniotic infection, and the unique expression signature is an extra peak in the 10 to 11 kDa molecular weight range in the test sample, which is indicative of intra-amniotic infection.

In a different embodiment, the proteomic profile is produced by Western blot analysis.

In another embodiment, the biological fluid is that of a human, and the proteomic profile includes information of the expression of one or more of the proteins selected from the group consisting of: macrophage capping protein, neutrophil gelatinase-associated lipocalin, myeloperoxidase; L-plastin; azurocidin; antibacterial protein FALL-39; Gp340 variant protein; Ebner salivary gland protein homologoue (GenBank Accession No. 355392) (SEQ ID NO: 12); leukocyte elastase inhibitor; calgranulin A; calgranulin B; cofilin; moesin; profilin I, cronin-like protein p57; annexin II, fibronectin; glia-derived nexin; antithrombin-III; squamous cell carcinoma antigen 1, squamous cell carcinoma antigen 2; serpin 12; cystatin A; cystatin B; cystatin C; IGFBP-1; Vitamin D-binding protein; apolipoprotein A-I; 14-3-3 protein sigma; 14-3-3 protein zeta/delta; gelsolin; lactotransferrin; phosphoglycerate kinase 1; phosphoglycerate mutase 1; and transketolase; or a fragment, precursor, or naturally occurring variant thereof.

In a further embodiment, the proteomic profile includes information of the expression of one or more of the proteins selected from the group consisting of macrophage capping protein; neutrophil gelatinase-associated lipocalin; myeloperoxidase; L-plastin; azurocidin; antibacterial protein FALL-39; leukocyte elastase inhibitor; calgranulin A; calgranulin B; profilin I, glia-derived nexin; serpin 12; cystatin A; and IGFBP-1; or a fragment, precursor, or naturally occurring variant thereof.

The foregoing method is suitable for the diagnosis of various fetal and maternal conditions, including, without limitation, intra-amniotic infection, developmental defects, including defects of an organ system, musculoskeletal deformities, and conditions resulting from chromosomal aneuploidies, such as Down_syndrome, trisomy-13, trisomy-18, Turner syndrome, or Klinefelter syndrome.

If the proteomic profile of the test sample is essentially the same as the proteomic profile of the normal sample, the subject is determined to be free of the maternal or fetal condition.

If the proteomic profile contains essentially the same unique expression signature as a diseased sample, the patient is diagnosed with the corresponding materal or fetal condition.

In another aspect, the invention concerns a method for the diagnosis of intra-amniotic infection, comprising (a) comparing the proteomic profile of a test sample of a biological fluid obtained from a pregnant female mammal with the proteomic profile of a normal sample, or a reference proteomic profile, wherein the proteomic profiles provide information of the mass of the proteins present in the samples, or the proteolytic fragments thereof; and (b) diagnosing the mammal with intra-amniotic infection if the proteomic profile of the test sample shows a unique expression signature in the 3–5 and/or 10–12 KDa molecular weight range.

In a further aspect, the invention concerns a method for the diagnosis of intra-amniotic infection, comprising:

(a) comparing the proteomic profile of a test sample of a biological fluid obtained from a pregnant female mammal with the proteomic profile of a normal sample; and (b) diagnosing the mammal with intra-amniotic infection if at least one protein selected from the group consisting of IGFB-1, profilin, ceruloplasmin, L-plastin, and calgraulin, or a fragment, precursor or naturally occurring variant thereof, is differentially expressed in the test sample relative to the normal sample.

In a particular embodiment, at least one of IGFBP-1, profilin, ceruloplasmin, and calgranulin, or a fragment, precursor, or naturally-occurring variant thereof, is overexpressed in the test sample relative to the normal sample.

In another embodiment, L-plastin is underexpressed in the test sample relative to the normal sample.

In yet another embodiment, the presence of IGFBP-1 is detected by identifying the proteolytic fragment shown in FIG. 12, or a fragment thereof.

In another aspect, the invention concerns a method for the diagnosis of a chromosomal aneuploidy, comprising:

(a) comparing the proteomic profile of a test sample of a biological fluid obtained from a pregnant female mammal with the proteomic profile of a normal sample, or a reference proteomic profile, wherein the proteomic profiles provide information of the mass of the proteins present in the samples, or the proteolytic fragments thereof; and (b) diagnosing the mammal with the chromosomal aneuploidy if the proteomic profile of the test sample shows a unique expression signature in the 4 to 15 KDa molecular weight range.

In a different aspect, the invention concerns a method for the diagnosis of a developmental defect of a fetus, comprising:

(a) comparing the proteomic profile of a test sample of a biological fluid obtained from a pregnant female mammal with the proteomic profile of a normal sample, or a reference proteomic profile; and (b) confirming the presence of the developmental defect if at least one actin-modulating protein, or a fragment, precursor, or naturally occurring variant thereof, is differentially expressed in the test sample relative to the normal sample.

In a particular embodiment of this method, the actin-modulating protein is selected from the group consisting of moesin, p57, gelsolin, and a 14-3-3 protein.

In a further aspect, the invention concerns a method for the diagnosis of a maternal or fetal infection or immune-response related disorder, comprising (a) comparing the proteomic profile of a test sample of a biological fluid obtained from a pregnant female mammal with the proteomic profile of a normal sample, or a reference proteomic profile; and (b) confirming the presence of the maternal or fetal infection or immune-response related disorder, if at least one protein selected from the group consisting of macrophage capping protein (MCP), leukocyte elastase, neutrophil gelatinase-associated lipcalcin (NGAL), myeloperoxidase, L-plastin, calgranulin, FALL-39, azyrocidin (CAP37), proteases and protease inhibitors, is differentially expressed in the test sample relative to the normal sample.

In a still further aspect, the invention concerns a method for the diagnosis of neonatal sepsis, comprising detecting in the proteomic profile of a biological fluid obtained from a pregnant females mammal the presence of Gp-340.

In yet another aspect, the invention concerns a proteomic profile of a biological fluid comprising information of one or more proteins selected from the group consisting of macrophage capping protein, neutrophil gelatinase-associated lipocalin, myeloperoxidase; L-plastin; azurocidin; antibacterial protein FALL-39; Gp340 variant protein; Ebner salivary gland protein homologoue (GenBank Accession No. 355392) (SEQ ID NO: 12; leukocyte elastase inhibitor; calgranulin A; calgranulin B; cofilin; moesin; profilin I, cronin-like protein p57; annexin II, fibronectin; glia-derived nexin; antithrombin-III; squamous cell carcinoma antigen 1, squamous cell carcinoma antigen 2; serpin 12; cystatin A; cystatin B; cystatin C; IGFBP-1; Vitamin D-binding protein; apolipoprotein A-I; 14-3-3 protein sigma; 14-3-3 protein zeta/delta; gelsolin; lactotransferrin; phosphoglycerate kinase 1; phosphoglycerate mutase 1; and transketolase; or a fragment, precursor, or naturally occurring variant thereof.

In a further aspect, the invention concerns a proteomic profile of a biological fluid comprising information of one or more proteins selected from the group consisting of macrophage capping protein; neutrophil gelatinase-associated lipocalin; myeloperoxidase; L-plastin; azurocidin; antibacterial protein FALL-39; leukocyte elastase inhibitor; calgranulin A; calgranulin B; profilin I, glia-derived nexin; serpin 12; cystatin A; and IGFBP-1; or a fragment, precursor, or naturally occurring variant thereof.

The invention further concerns a proteomic profile of a biological fluid characteristic of intra-amniotic infection, comprising information confirming the presence of a protein selected from the group consisting of IGFB-1, profilin, ceruloplasmin, L-plastin, and calgraulin.

In another aspect, the invention concerns a proteomic profile of a biological fluid characteristic of intra-amniotic infection represented in a form providing information of the molecular weight of proteins present in the biological fluid, or the proteolytic fragments thereof, comprising a unique expression signature in the 3–5 KDa and/or 10–12 KDa molecular weight range.

In a further aspect, the invention concerns the proteomic profile essentially as shown in any one of FIGS. 1A–1C, or essentially as shown in any one of FIGS. 2A–C, or essentially as shown in any one of FIGS. 3A–C, or essentially as shown in FIG. 4A or 4B, or essentially as shown in any one of FIGS. 6–10.

In a particular embodiment, the proteomic profile is analyzed in a microarray format.

BRIEF DESCRIPTION OF THE DRAWINGS

FIGS. 2A–C. Time course analyses of the primate amniotic fluid in response to infection (GBS). Amniotic fluid was collected before the inoculation of bacteria and serially after infection and subjected to SELDI-TOF analysis as described below. FIG. 2 A: before infection; 2B: 12 hours after infection; 2C: 36 hours after infection.

FIG. 5 SDS-PAGE Commassie Blue stained gel. A) 4 human control AF samples pooled; B) individual control AF sample; C) 4 human infected AF samples pooled; D) individual infected AF sample.

FIG. 6 Detection of differential protein expression in the human amniotic fluid. A) Control AF sample (pooled); B) Infected AF sample (pooled).

FIG. 7 Detection of differential protein expression in the human amniotic fluid. A) Control AF sample (pooled); B) Infected AF sample (pooled).

FIG. 11 Schematic representation of de novo protein sequence identification of amniotic fluid proteins. PRO1_HUMAN (P07737) Profilin I. (SEQ ID Nos. 5–11).

FIG. 12 IGFBP-1 de novo protein identification and proteolytic fragment sequence (SEQ ID No. 1). The peptide sequences found in samples 0426se_H1_12 and 0425se_H1_13 with the Ms/MS are shown in lower case (SEQ ID Nos: 2 and 3). These came from infected amniotic fluid when run on 1-D gel bands that were trypsin digested and subjected to MS/MS analysis. The proteolytic fragment of IGF-BP-1 detected in 1-D gels (low molecular weight range, FIG. 5), Western blots (FIG. 6) and MS/MS analysis (FIG. 13) of trypsin-digested ~10.5 to 12 KDa band from infected amniotic fluid is represented in the region of the underlined sequence (SEQ ID No: 4).

DETAILED DESCRIPTION OF THE PREFERRED EMBODIMENT

A. Definitions

Figure 1A:
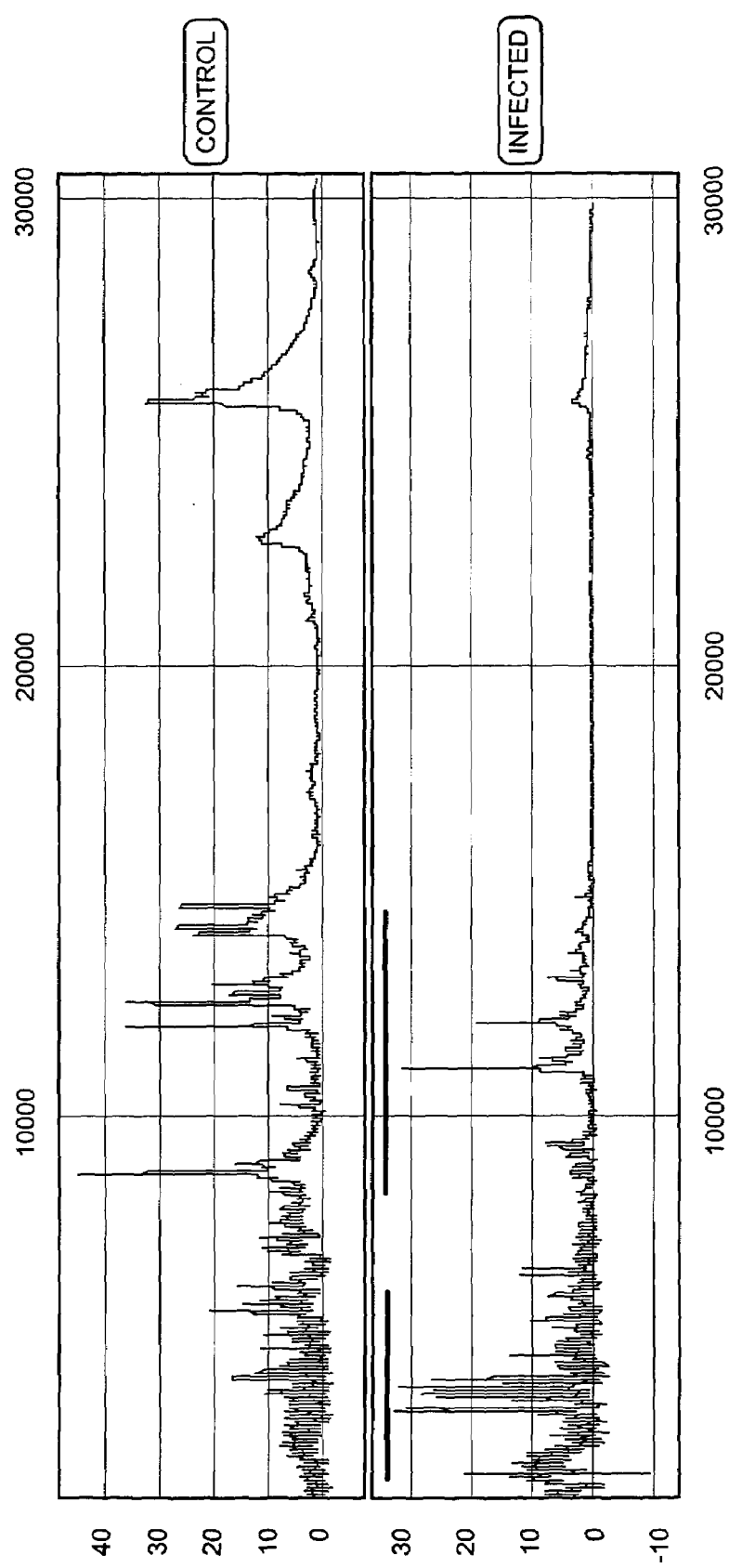
FIGS. 1A–C. Infection-induced differential protein expression in the primate amniotic fluid. SELDI-TOF analysis of amniotic fluid extracts bound to chemically defined Normal Phase chip arrays. A). Whole spectrum collected at 235 laser intensity showing the differences in the peak intensities. B) Detailed spectrum showing the differences in the 10 to 12 KDa region between control and infected. C) Detailed spectrum showing the differences in the 3–5 KDa region between control and infected. Solid lines were used to show the significant differences in expression (unique expression signatures) which could be used to develop diagnostic tests.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994) provides one skilled in the art with a general guide to many of the terms used in the present application.

The term "proteome" is used herein to describe a significant portion of proteins in a biological sample at a given time. The concept of proteome is fundamentally different from the genome. While the genome is virtually static, the proteome continually changes in response to internal and external events.

The term "proteomic profile" is used to refer to a representation of the expression pattern of a plurality of proteins in a biological sample, e.g. a biological fluid at a given time. The proteomic profile can, for example, be represented as a mass spectrum, but other representations based on any physicochemical or biochemical properties of the proteins are also included. Thus the proteomic profile may, for example, be based on differences in the electrophoretic properties of proteins, as determined by two-dimensional gel electrophoresis, e.g. by 2-D PAGE, and can be represented, e.g. as a plurality of spots in a two-dimensional electrophoresis gel. Differential expression profiles may have important diagnostic value, even in the absence of specifically identified proteins. Single protein spots can then be detected, for example, by immunoblotting, multiple spots or proteins using protein microarrays. The proteomic profile typically represents or contains information that could range from a few peaks to a complex profile representing 50 or more peaks. Thus, for example, the proteomic profile may contain or represent at least 2, or at least 5 or at least 10 or at least 15, or at least 20, or at least 25, or at least 30, or at least 35, or at least 40, or at least 45, or at least 50 proteins.

The term "pathologic condition" is used in the broadest sense and covers all changes and phenomena that compromise the well-being of a subject. Pathologic maternal conditions include, without limitation, intra-amniotic infection, conditions of fetal or maternal origin, such as, for example preeclampsia, and preterm labor and delivery. Pathologic fetal conditions include, without limitation, chromosomal defects (aneuploidies), such as Down_syndrome, and all abnormalities in gestational age and fetal maturity.

The term "state of a pathologic [maternal or fetal] condition" is used herein in the broadest sense and refers to the absence, presence, extent, stage, nature, progression or regression of the pathologic condition.

The term "unique expression signature" is used to describe a unique feature or motif within the proteomic profile of a biological sample (e.g. a reference sample) that differs from the proteomic profile of a corresponding normal biological sample (obtained from the same type of source, e.g. biological fluid) in a statistically significant manner.

The terms "intra-amniotic infection (IAI)," "amniotic fluid infection," "amnionitis," and "clinical chorioamnionitis" are used interchangeably, and refer to an acute infection, including, but not restricted to bacterial, of the amniotic fluid and intrauterine contents during pregnancy.

"Patient response" can be assessed using any endpoint indicating a benefit to the patient, including, without limitation, (1) inhibition, at least to some extent, of the progression of a pathologic condition, (2) prevention of the pathologic condition, (3) relief, at least to some extent, of one or more symptoms associated with the pathologic condition; (4) increase in the length of survival following treatment; and/or (5) decreased mortality at a given point of time following treatment.

The term "treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Congenital malformation" is an abnormality which is non-hereditary but which exists at birth.

B. Detailed Description

The present invention concerns methods and means for an early, reliable and non-invasive testing of maternal and fetal conditions based upon the proteomic profile of a biological fluid of the mother or fetus. The invention utilizes proteomics techniques well known in the art, as described, for example, in the following textbooks, the contents of which are hereby expressly incorporated by reference: *Proteome Research: New Frontiers in Functional Genomics (Principles and Practice)*, M. R. Wilkins et al., eds., Springer Verlag, 1007; *2-D Proteome Analysis Protocols*, Andrew L Link, editor, Humana Press, 1999; *Proteome Research: Two-Dimensional Gel Electrophoresis and Identification Methods (Principles and Practice)*, T. Rabilloud editor, Springer Verlag, 2000; *Proteome Research: Mass Spectrom-* etry (*Principles and Practice*), P. James editor, Springer Verlag, 2001; *Introduction to Proteomics*, D. C. Liebler editor, Humana Press, 2002; *Proteomics in Practice: A Laboratory Manual of Proteome Analysis*, R. Westermeier et al., eds., John Wiley & Sons, 2002.

One skilled in the art will recognize many methods and materials similar or equivalent to those described herein, which could be used in the practice of the present invention. Indeed, the present invention is in no way limited to the methods and materials described.

1. Identification of proteins and Polypeptides Expressed in Biological Fluids

According to the present invention, proteomics analysis of biological fluids can be performed using a variety of methods known in the art.

Typically, protein patterns (proteome maps) of samples from different sources, such as normal biological fluid (normal sample) and a test biological fluid (test sample), are compared to detect proteins that are up- or down-regulated in a disease. These proteins can then be excised for identification and full characterization, e.g. using peptide-mass fingerprinting and/or mass spectrometry and sequencing methods, or the normal and/or disease-specific proteome map can be used directly for the diagnosis of the disease of interest, or to confirm the presence or absence of the disease.

In comparative analysis, it is important to treat the normal and test samples exactly the same way, in order to correctly represent the relative abundance of proteins, and obtain accurate results. The required amount of total proteins will depend on the analytical technique used, and can be readily determined by one skilled in the art. The proteins present in the biological samples are typically separated by two-dimensional gel electrophoresis (2-DE) according to their pI and molecular weight. The proteins are first separated by their charge using isoelectric focusing (one-dimensional gel electrophoresis). This step can, for example, be carried out using immobilized pH-gradient (IPG) strips, which are commercially available. The second dimension is a normal SDS-PAGE analysis, where the focused IPG strip is used as the sample. After 2-DE separation, proteins can be visualized with conventional dyes, like Coomassie Blue or silver staining, and imaged using known techniques and equipment, such as, e.g. BIO-RAD GS800™ densitometer and PDQUEST™ software, both of which are commercially available. Individual spots are then cut from the gel, destained, and subjected to tryptic digestion. The peptide mixtures can be analyzed by mass spectrometry (MS). Alternatively, the peptides can be separated, for example by capillary high pressure liquid chromatography (HPLC) and can be analyzed by MS either individually, or in pools.

Mass spectrometers consist of an ion source, mass analyzer, ion detector, and data acquisition unit. First, the peptides are ionized in the ion source. Then the ionized peptides are separated according to their mass-to-charge ratio in the mass analyzer and the separate ions are detected. Mass spectrometry has been widely used in protein analysis, especially since the invention of matrix-assisted laser-desorption ionisation/time-of-flight (MALDI-TOF) and electrospray ionisation (ESI) methods. There are several versions of mass analyzer, including, for example, MALDI-TOF and triple or quadrupole-TOF, or ion trap mass analyzer coupled to ESI. Thus, for example, a Q-Tof-2 mass spectrometer utilizes an orthogonal time-of-flight analyzer that allows the simultaneous detection of ions across the full mass spectrum range. For further details see, e.g. Chemusevich et al., *J. Mass Spectrom.* 36:849–865 (2001).

If desired, the amino acid sequences of the peptide fragments and eventually the proteins from which they derived can be determined by techniques known in the art, such as certain variations of mass spectrometry, or Edman degradation.

2. Fetal-Maternal Conditions Benefiting from Early and Non-Invasive Diagnosis a. Intra-Amniotic Infection Intra-amniotic infection (IAI) is an acute bacterial infection of the amniotic fluid and intrauterine contents during pregnancy. Prospective studies indicate that IAI occurs in 4% to 10% of all deliveries (Newton, E. R., Prihoda, T. J., and Gibbs, R. S.: Logistic regression analysis of risk factors for intra-amniotic infection. *Obstet.Gynecol.* 73:571, 1989; Soper, D. E., Mayhall, C. G., and Dalton, H. P.: Risk factors for intraamniotic infection: a prospective epidemicologic study. *American Journal of Obstetrics and Gynecology* 161:562, 1989; and Lopez-Zeno, J. A., Peaceman, A. M., Adashek, J. A., and Socol, M. L.: A controlled trial of a program for the active management of labor. *N. Engl. J. Med.* 326:450, 1992). Other terms used to describe IAI include amniotic fluid infection, amnionitis, and clinical chorioamnionitis. Intra-amniotic infection is clinically diagnosed by maternal fever, uterine tenderness, leukocytosis, and fetal tachycardia and should be distinguished from histologic chorioamnionitis. Intra-amniotic infection is an important cause of maternal and neonatal morbidity. Intra-amniotic infection accounts for 10–40% of cases of febrile morbidity in the peripartum period and is associated with 20–40% of cases of early neonatal sepsis and pneumonia (Newton, E. R.: Chorioamnionitis and intraamniotic infection. *Clin.Obstet.Gynecol.* 36:795, 1993). Maternal bacteremia occurs in 2–6% of patients with IAI and postpartum infectious morbidity is increased. There is also an increased risk of dysfunctional labor and cesarean delivery among patients with IAI. Duff et al. reported a 75% incidence of dysfunctional labor and a 34% incidence of cesarean delivery among patients who developed intra-amniotic infection while in labor (Duff, P., Sanders, R., and Gibbs, R. S.: The course of labor in term pregnancies with chorioamnionitis. *American Journal of Obstetrics and Gynecology* 147:391, 1983). Intra-amniotic infection is also associated with increased neonatal morbidity and mortality, particularly among preterm neonates. In general, there is a three to four-fold increase in perinatal mortality among low birth weight neonates born to mothers with IAI (Gibbs, R. S., Castillo, M. A., and Rodgers, P. J.: Management of acute chorioamnionitis. *American Journal of Obstetrics and Gynecology* 136:709, 1980; Gilstrap, L. C., III, Leveno, K. J., Cox, S. M., Burris, J. S., Mashburn, M., and Rosenfeld, C. R.: Intrapartum treatment of acute chorioamnionitis: impact on neonatal sepsis. *Am. J. Obstet. Gynecol,* 159:579, 1988). There are also increases in respiratory distress syndrome, intraventricular hemorrhage, and neonatal sepsis Morales, W. J.: The effect of chorioamnionitis on the developmental outcome of preterm infants at one year. *Obstetrics and Gynecology* 70:183, 1987). Recently, IAI has been implicated in neonatal periventricular leukomalacia and cerebral palsy; the risks of cerebral white matter damage and cerebral palsy are nine-fold greater in the setting of intra-amniotic infection Bejar, R., Wozniak, P., Allard, M., Benirschke, K., Vaucher, Y., Coen, R., Berry, C., Schragg, P., Villegas, I., and Resnik, R.: Antenatal origin of neurologic damage in newborn infants. I. Preterm infants. *Am. J. Obstet. Gynecol.* 159:357, 1988; Grether, J. K. and Nelson, K. B.: Maternal infection and cerebral palsy in infants of normal birth weight. *JAMA* 278:207, 1997). Finally, subclinical IAI has been found in at least 10% of women in preterm labor with intact fetal membranes, suggesting that IAI is an important, and potentially preventable, cause of prematurity (Romero, R., Avila, C., Brekus, C. A., and Morotti, R.: The role of systemic and intrauterine infection in preterm parturition. *Annuals of the New York Academy of Sciences* 622:355, 1991). A literature review by Newton demonstrated incidences of clinical IAI of 41% at gestational ages less than 27 weeks, 15% at gestational ages of 27–37 weeks, and 2% at gestations of 38 weeks or greater (Newton et al., supra). Bacteria indigenous to the lower genital tract have also been recovered from the amniotic fluid of 10–20% of all women in preterm labor with intact fetal membranes without clinical signs of intraamniotic infection (Romero et al., supra), and in up to 67% of women in preterm labor with pregnancies ending at 23–24 weeks (Watts, D. H., Krohn, M. A., Hillier, S. L., and Eschenbach, D. A.: The association of occult amniotic fluid infection with gestational age and neonatal outcome among women in preterm labor. *Obstet Gynecol* 79:351, 1992). Most of these patients deliver rapidly, and clinically apparent IAI develops in many. These observations support the hypothesis that ascending, initially subclinical intrauterine infections precede preterm labor and may be an important cause of extreme preterm deliveries.

b. Preeclampsia

Preeclampsia, defined as maternal hypertension accompanied by proteinuria, edema, or both, occurs in 7% of pregnancies not terminating in the first trimester. Although the cause is unknown, it is more common in extremes of age in childbearing, maternal diabetes, pregnancies with multiple gestations, and pre-existing maternal renal disease and or hypertension. Preeclampsia is associated with increases in perinatal mortality, and may also lead to eclampsia, characterized by maternal seizures and increased maternal mortality. Currently the mainstay of therapy for preeclampsia is delivery and anticonvulsant prophylaxis with magnesium sulfate. Prior to the advent of magnesium sulfate therapy, the observed maternal mortality was 20–30%. However, with prompt diagnosis, allowing anticonvulsant therapy with magnesium sulfate, anti-hypertensives, and delivery the maternal mortality has been reduced to near zero.

Unfortunately, the diagnosis of preeclampsia based upon commonly recognized symptoms and signs is frequently difficult, and occurs late in the course of the disease. Frequently fetal compromise in growth or well-being is the first recognized manifestation of preeclampsia. Laboratory markers for preeclampsia include quantitation of proteinuria, and elevated serum concentrations of uric acid or creatinine. There are no currently available serum markers for early preeclampsia or markers which identify women which will develop preeclampsia. Recently prospective serum markers including leptin and uric acid have been associated with subsequent preeclampsia in one study (Gursoy T, et al. Preeclampsia disrupts the normal physiology of leptin.: Am J Perinatol.19(6):303–10, 2002) but much work is needed to confirm these findings. Development of early and reliable markers for preeclampsia is imperative to allow for therapy and intervention to optimize the outcome for the neonate and mother.

c. Preterm Labor and Delivery

Preterm delivery is defined as birth prior to the $37^{th}$ completed week of gestation. The incidence of preterm birth in the United States is 10–11% of all live births, and is increasing despite aggressive treatment of preterm labor. Overall, prematurity and its consequences are responsible for 80% of perinatal deaths not attributable to congenital malformations and add approximately $5 billion annually to the national health care budget. Risk factors for preterm birth include non-white race, young age, low socioeconomic status, maternal weight below 55 kg, nulliparity, $1^{st}$ trimester bleeding, multiple gestations (Meis P J, Michielutte R, Peters T J, et al. Factors associated with preterm birth in Cardiff, Wales: II. Indicated and spontaneous preterm birth. *Am J Obstet Gynecol* 173:597–602, 1995)

Unfortunately the prediction of patients at risk for spontaneous preterm birth has been generally disappointing (Creasy R K, Iams J D. Preterm labor and delivery. In *Maternal-Fetal Medicine*, Creasy R K, Resnik R (eds.). W. B. Saunders Company, Philadelphia, Pa. $4^{th}$ edition, 1999. Pages 498–531). Previous attempts at defining the population at greatest risk for preterm birth, and thereby potentially benefiting from early intervention have included risk-scoring indices, biochemical detection of cervical fetal fibronectin, ultrasound measurement of cervical length, and home uterine activity monitoring. These programs have been both costly, and have been hampered by the inability to predict with accuracy which patients might benefit from early intervention or prophylaxis. All suffer from poor positive predictive value of approximately 30%, with the majority of patients identified as "at risk" delivering at term. Interventions, including pharmacologic treatment to inhibit uterine contractions, are efficacious, but depend upon the early and reliable diagnosis of preterm labor. Early and reliable markers to identify patients at greatest risk for preterm birth are therefore necessary to reduce the tremendous costs and neonatal mortality and morbidity associated with preterm birth.

d. Chromosomal Aneuploidies

Chromosomal abnormalities are a frequent cause of perinatal morbidity and mortality. Chromosomal abnormalities occur with an incidence of 1 in 200 live births. The major cause of these abnormalities is chromosomal aneuploidy, an abnormal number of chromosomes inherited from the parents. One of the most frequent chromosomal aneuploidies is trisomy-21 (Down syndrome), which has an occurrence of 1 in 800 live births (Hook E B, Hamerton J L: The frequency of chromosome abnormalities detected in consecutive newborn studies: Differences between studies: Results by sex and by severity of phenotypic involvement. In Hook E B, Porter I H (eds): Population Cytogenetics, pp 63–79. New York, Academic Press, 1978). The primary risk factor for trisomy-21 is maternal age greater than 35, but 80% of children with trisomy-21 are born to women younger than 35 years of age. Other common aneuploidic conditions include trisomies 13 and 18, Turner Syndrome and Klinefelter syndrome.

Because 80% of children with trisomy-21 are born to women younger than 35 years of age, prenatal diagnostic screening programs designed on the basis of maternal age alone are inefficient. Prenatal screening programs have therefore been supplemented with maternal serum screening for analytes associated with fetal chromosomal aneuploidy, ultrasound, or a combination of both. Candidate serum markers that have been widely utilized include alpha-fetoprotein (AFP), unconjugated estriol, human choriogonadotrophic hormone (hHCG), and inhibin-A. However, with a screen positive rate of 2–5%, the detection rate for trisomy-21 and other aneuploidies has been disappointing, with detection rates of only 70–86% (Cuckle H. Biochemical screening for Down syndrome. Eur J Obstet Gynecol Reprod Biol. 92(1):97–101, 2000). Further, the rate of true positive tests, i.e., trisomy-21 among those with a screen positive test is only 1–2%, resulting in an overall false positive rate in excess of 98%.

The definitive diagnosis of chromosomal aneuploidies following maternal serum screening and ultrasound requires a mid-trimester genetic amniocentesis. This is an invasive procedure associated with a 0.5% risk of loss of the pregnancy. Further, chromosomal analysis of amniotic fluid cells is a labor-intensive and time consuming procedure, taking up to 2 weeks. Reliable tests are therefore necessary to improve the detection of chromosomal aneuploidies from maternal serum, reduce the unacceptably high false positive rate of maternal screening, and increase the speed and efficiency of diagnosis from amniotic fluid following amniocentesis.

3. Diagnosis of Maternal/Fetal Conditions Using the Proteomic Profile of Biological Fluids The present invention provides an early and reliable, non-invasive method for the diagnosis of the foregoing and other similar maternal/fetal conditions by proteomic analysis of biological fluids, such as, for example, amniotic fluid, serum, plasma, urine, cerebrospinal fluid, breast milk, mucus, or saliva.

As noted before, in the context of the present invention the term "proteomic profile" is used to refer to a representation of the expression pattern of a plurality of proteins in a biological sample, e.g. a biological fluid at a given time. The proteomic profile can, for example, be represented as a mass spectrum, but other representations based on any physicochemical or biochemical properties of the proteins are also included. Although it is possible to identify and sequence all or some of the proteins present in the proteome of a biological fluid, this is not necessary for the diagnostic use of the proteomic profiles generated in accordance with the present invention. Diagnosis of a particular disease can be based on characteristic differences (unique expression signatures) between a normal proteomic profile, and proteomic profile of the same biological fluid obtained under the same circumstances, when the disease or pathologic condition to be diagnosed is present. The unique expression signature can be any unique feature or motif within the proteomic profile of a test or reference biological sample that differs from the proteomic profile of a corresponding normal biological sample obtained from the same type of source, in a statistically significant manner. For example, if the proteomic profile is presented in the form of a mass spectrum, the unique expression signature is typically a peak or a combination of peaks that differ, qualitatively or quantitatively, from the mass spectrum of a corresponding normal sample. Thus, the appearance of a new peak or a combination of new peaks in the mass spectrum, or any statistically significant change in the amplitude or shape of an existing peak or combination of existing peaks in the mass spectrum can be considered a unique expression signature. When the proteomic profile of the test sample obtained from a mammalian subject is compared with the proteomic profile of a reference sample comprising a unique expression signature characteristic of a pathologic maternal or fetal condition, the mammalian subject is diagnosed with such pathologic condition if it shares the unique expression signature with the reference sample.

A particular pathologic maternal/fetal condition can be diagnosed by comparing the proteomic profile of a biological fluid obtained from the subject to be diagnosed with the proteomic profile of a normal biological fluid of the same kind, obtained and treated the same manner. If the proteomic profile of the test sample is essentially the same as the proteomic profile of the normal sample, the subject is considered to be free of the subject pathologic maternal/fetal condition. If the proteomic profile of the test sample shows a unique expression signature relative to the proteomic profile of the normal sample, the subject is diagnosed with the maternal/fetal condition in question.

Alternatively or in addition, the proteomic profile of the test sample may be compared with the proteomic profile of a reference sample, obtained from a biological fluid of a subject independently diagnosed with the pathologic maternal/fetal condition ion question. In this case, the subject is diagnosed with the pathologic condition if the proteomic profile of the test sample shares at least one feature, or a combination of features representing a unique expression signature, with the proteomic profile of the reference sample.

In the methods of the present invention the proteomic profile of a normal biological sample plays an important diagnostic role. As discussed above, if the proteomic profile of the test sample is essentially the same as the proteomic profile of the normal biological sample, the patient is diagnosed as being free of the pathologic maternal/fetal condition to be identified. This "negative" diagnosis is of great significance, since it eliminates the need of subjecting a patient to unnecessary treatment or intervention, which could have potential side-effects, or may otherwise put the patient, fetus, or neonate at risk. The data are analyzed to determine if the differences are statistically significant.

The sensitivity of the diagnostic methods of the present invention can be enhanced by removing the proteins found both in normal and diseased proteome at essentially the same expression levels (common proteins, such as albumin and immunoglobulins) prior to analysis using conventional protein separation methods. The removal of such common proteins, which are not part of the unique expression signature, results in improved sensitivity and diagnostic accuracy. Alternatively or in addition, the expression signatures of the common proteins can be eliminated (or signals can be removed) during computerized analysis of the results, typically using spectral select algorithms, that are machine oriented, to make diagnostic calls.

The results detailed in the Examples below present proteomic profiles characteristics of intraamniotic infection (IAI) that differ from the normal proteomic profile of amniotic fluid in a statistically significant manner. In addition, the Examples present expression markers and unique expression signatures characteristic of IAI and Down syndrome, respectively.

Statistical methods for comparing proteomic profiles are well known in the art. For example, in the case of a mass spectrum, the proteomic profile is defined by the peak amplitude values at key mass/charge (M/Z) positions along the horizontal axis of the spectrum. Accordingly, a characteristic proteomic profile can, for example, be characterized by the pattern formed by the combination of spectral amplitudes at given M/Z vales. The presence or absence of a characteristic expression signature, or the substantial identity of two profiles can be determined by matching the proteomic profile (pattern) of a test sample with the proteomic profile (pattern) of a reference or normal sample, with an appropriate algorithm. A statistical method for analyzing proteomic patterns is disclosed, for example, in Petricoin III, et al., *The Lancet* 359:572–77 (2002).; Issaq et al., *Biochem Biophys Commun* 292:587–92 (2002); Ball et al., *Bioinformatics* 18:395–404 (2002); and Li et al., *Clinical Chemistry Journal*, 48:1296–1304 (2002).

4. Screening Assays

The proteomic profiles of the invention find further utility in screening assays to identify drug candidates for the treatment of a particular maternal/fetal condition. Such screening assays are based on the ability of a test molecule to convert a proteomic profile containing an expression signature characteristic of the maternal/fetal condition to be treated into a proteomic profile devoid of the expression signature. In one particular embodiment, the ability of the test compound to convert a pathologic expression profile into a normal expression profile is tested. In another embodiment, the screening assay tests the ability of a test compound to convert a unique expression signature characteristic of a pathologic condition into a corresponding normal expression signature.

Such screening assays can be performed in vitro by treatment of a diseased biological sample and comparing the proteomics expression profiles before and after treatment. Alternatively or in addition, drug screening can be performed by treating a laboratory animal exhibiting the target pathologic maternal/fetal condition with a test compound, taking samples of a biological fluid of the animal before and after treatment, and comparing the proteomic profiles of the two samples. In this assay, it is also possible to take samples of biological fluid at various time points following treatment, and follow the time course of treatment. These methodologies may be applied also to characterize the toxicology of pharmaceutical agents, as well as to identify optimal candidates for specific therapies.

The test compounds can, for example, be peptides, non-peptide small organic molecules, proteins, polypeptides, antibodies (including antibody fragments), antisense molecules, oligonucleotide decoys, and any other classes of molecules that have been used previously as drugs or drug candidates.

The biological fluid can, for example, be amniotic fluid, serum (e.g. maternal serum), plasma, urine, cerebrospinal fluid, breast milk, mucus, or saliva.

Therapeutically active compounds identified can be formulated in conventional pharmaceutical formulations. A compendium of art-known formulations is found in *Remington's Pharmaceutical Sciences*, latest edition, Mack Publishing Company, Easton, Pa. Reference to this manual is routine in the art.

5. Protein Arrays

Both the diagnostic and the screening assays discussed above can be performed using protein arrays. In recent years, protein arrays have gained wide recognition as a powerful means to detect proteins, monitor their expression levels, and investigate protein interactions and functions. They enable high-throughput protein analysis, when large numbers of determinations can be performed simultaneously, using automated means. In the microarray or chip format, that was originally developed for DNA arrays, such determinations can be carried out with minimum use of materials while generating large amounts of data.

Although proteome analysis by 2D gel electrophoresis and mass spectrometry, as described above, is very effective, it does not always provide the needed high sensitivity and this might miss many proteins that are expressed at low abundance. Protein microarrays, in addition to their high efficiency, provide improved sensitivity.

Protein arrays are formed by immobilizing proteins on a solid surface, such as glass, silicon, micro-wells, nitrocellulose, PVDF membranes, and microbeads, using a variety of covalent and non-covalent attachment chemistries well known in the art. The solid support should be chemically stable before and after the coupling procedure, allow good spot morphology, display minimal nonspecific binding, should not contribute a background in detection systems, and should be compatible with different detection systems.

In general, protein microarrays use the same detection methods commonly used for the reading of DNA arrays. Similarly, the same instrumentation as used for reading DNA microarrays is applicable to protein arrays.

Thus, capture arrays (e.g. antibody arrays) can be probed with fluorescently labelled proteins from two different sources, such as normal and diseased biological fluids. In this case, the readout is based on the change in the fluorescent signal as a reflection of changes in the expression level of a target protein. Alternative readouts include, without limitation, fluorescence resonance energy transfer, surface plasmon resonance, rolling circle DNA amplification, mass spectrometry, resonance light scattering, and atomic force microscopy.

For further details, see, for example, Zhou H, et al., *Trends Biotechnol.* 19:S34–9 (2001); Zhu et al., *Current Opin. Chem. Biol.* 5:40–45-(2001); Wilson and Nock, *Angew Chem Int Ed Engl* 42:494–500 (2003); and Schweitzer and Kingsmore, *Curr Opin Biotechnol* 13:14–9 (2002). Biomolecule arrays are also disclosed in U.S. Pat. No. 6,406,921, issued Jun. 18, 2002, the entire disclosure of which is hereby expressly incorporated by reference.

Further details of the invention will be apparent from the following non-limiting examples.

EXAMPLE 1

General Protocols

Primate Model of Intra-amniotic Infection

This protocol was approved by the Institutional Animal Care Utilization Committee of the Oregon National Primate Research Center, and guidelines for humane care were followed. Three pregnant rhesus monkeys (*Macaca mulatta*) with timed gestations were chronically catheterized as previously described (Haluska G J, et al., Temporal changes in uterine activity and prostaglandin response to RU 486 in rhesus macaques in late gestation., *Am J Obstet Gynecol* 157: 1487–95 (1987); and Gravett M G, et al., An experimental model for intramniotic infection and preterm labor in rhesus monkeys. *Am J Obstet Gynecol* 171: 1660–7 (1994)). Briefly, at approximately day 110 of gestation (term is 167 days) pregnant animals were conditioned to a jacket and tether system (Ducssay C A, et al., Simplified vest and tether system for maintenance of chronically catheterized pregnant rhesus monkeys. *Lab. Anim Sci* 38:343–4 (1988)). After conditioning, intrauterine surgery was performed between days 119 and 126 of gestation under general anesthesia. Maternal femoral arterial and venous catheters, fetal arterial and venous catheters, two open-ended intra-amniotic pressure catheters, myometrial electromyographic electrodes, and fetal electrocardiographic electrodes were surgically implanted. All animals received terbutaline sulfate (1 mg intravenously over 3 to 5 hours twice daily) for 1 to 5 days after surgery to control uterine irritability. Animals also received cefazolin (250 mg intravenously every 12 hours), which was discontinued at least 48 hours before inoculation of bacteria.

After postoperative stabilization for 8 to 13 days (day 126 to 138 of gestation), intra-amniotic infection was established by intra-amniotic inoculation of $10^6$ colony-forming units (cfu) of group B Streptococcus, type III, grown in overnight cultures in Todd-Hewitt broth, centrifuged, washed, and suspended in 0.5 ml of saline solution (n=3 animals), $10^7$ cfu of *Ureaplasma urealyticum* (1 animal) or *Mycoplasma hominis* (1 animal), grown in broth. Amniotic fluid samples were collected serially from all animals during the study period (daily before inoculation and every 4 to 12 hours after inoculation) for quantitative bacterial cultures, white blood cell analysis by hemocytometer, and cytokine and prostaglandin concentrations (previously reported—Gravett MG, et al., An experimental model for intra-amniotic infection and preterm labor in rhesus monkeys. *Am J Obstet Gynecol* 171: 1660–7 (1994)).

Fetal electrocardiographic and uterine activity (electromyographic and intra-amniotic pressure) were continuously recorded from surgery until delivery. Uterine contractility was recorded as the area under the contraction curve per hour and expressed as the hourly contraction area (HCA) in millimeters of mercury times seconds/hour.

The maternal cervix was palpated vaginally before infection and serially thereafter. Consistency, effacement, and dilatation were recorded at each examination. After delivery, by cesarean section in all except one animal and vaginally in one animal, decidual, placental, and inter membrane bacterial cultures were obtained form infected animals to confirm infection and histopathologic studies were performed.

Amniotic Fluid Assays

Amniotic fluid samples (3 ml) were immediately centrifuged after collection at 3,000 rpm and 4° C. for 20 minutes. The sediment was saved for cellular analysis and the supernatant stored in pyrogen-free sterile vials at −20° C. until assayed.

Human Study

The study population was drawn from 309 women admitted in premature labor with intact fetal membranes to the University of Washington Medical Center or associated hospitals in Seattle between Jun. 25, 1991 and Jun. 30, 1997, as previously described (Hitti J, et al., Amniotic fluid tumor necrosis factor-α and the risk of respiratory distress syndrome among preterm infants. *Am J Obstet Gynecol* 177: 50–6 (1997)). All women provided written informed consent, and the study protocol was approved by the Institutional Review Boards for all participating hospitals. The participants were at gestational ages of 22 to 34 weeks by last menstrual period or from the earliest available ultrasound. All participants had intact fetal membranes at study enrollment. Preterm labor was defined as regular uterine contractions at a frequency of 10 minutes with either documented cervical change or a cervical dilatation of 1 centimeter or effacement of 50%. Women with cervical dilatation >4 centimeters or ruptured membranes at admission were excluded. Women with multiple gestations, cervical cerclage, placenta previa, abruptio placentae, diabetes, hypertension, and pre-eclampsia were considered eligible if they otherwise met study criteria.

Transabdominal amniocentesis was performed under ultrasound guidance for all study participants and maternal venous blood was also collected by venipuncture at the time of enrollment From this study population, a subset (Tables 1A and B) was retrospectively identified for proteomic analysis as reported here. This subset included 11 patients with evidence of intrauterine infection (as defined by the recovery of a microbial pathogen form amniotic fluid or an amniotic fluid IL-6 concentration of ≧2,000 pg/ml), and a randomly selected subset of 11 patients without intrauterine infection but with preterm birth and 11 patients without infection and with preterm labor responsive to tocolytic therapy and who had subsequent term birth. These patients constitute the study population for this report.

The study population was divided into three groups: 1) those patients with evidence of intrauterine infection, based upon either recovery of microorganisms from amniotic fluid or an amniotic fluid IL-6 concentration of >2,000 pg/ml; 2) those patients with preterm labor and delivery prior to 35 weeks of gestation without evidence of intrauterine infection; and 3) those patients with preterm labor responsive to tocolytic therapy who delivered at ≧35 weeks of gestation. There were no differences in maternal age, race, or parity between these three groups (Tables 1A and B). However, patients with intrauterine infection were seen at a somewhat earlier gestational age at enrollment (p=0.10) and delivered at a significantly earlier gestation age than those patients with preterm delivery without infection or those with term delivery (27.3+0.9 weeks versus 29.8+1.0 and 37.0+0.9 weeks respectively, p<0.0001). In addition, those with intrauterine infection had a significantly shorter enrollment to delivery interval (2.1±5.6 days, compared to 8.4±6.3 and 46.9±5.6 days for the other two groups, p<0.0001). Ninety-one percent of those with intrauterine infection delivered within seven days of enrollment.

Among those eleven patients with infection, microorganisms were recovered from four (2 with *Escherichia coli*, 1 with *Candida albicans*, and 1 with mixed anaerobes); all of these patients delivered within seven days. Seven other patients were identified based upon amniotic fluid IL-6 concentrations of greater than 2,000 pg/ml. The mean amniotic fluid concentration of interleukin-6 was 27.7±7.8 ng/ml among these patients, compared to 0.68±0.20 ng/ml among those with preterm delivery without infection and 0.25±0.13 ng/ml among those with preterm labor and term delivery (p<0.01).

TABLE 1A

Characteristics of the Study Population

| Characteristic | GROUP 1 PMD with IUI (n = 11) | GROUP 2 PMD without IUI (n = 11) | GROUP 3 PML with subsequent term delivery (n = 11) | GROUP 3 vs 1 p value |
|---|---|---|---|---|
| Maternal Age | 24.5 ± 5.4 | 26.6 ± 9.0 | 25.6 ± 6.0 | NS |
| White Race | 6(55%) | 4(36%) | 6(55%) | NS |
| Parity | 1.9 ± 1.6 | 1.9 ± 1.5 | 3.0 ± 2.5 | NS |
| Nulliparity | 3(27%) | 1(9%) | 1(9%) | NS |
| Gestational Age at Enrollment (wks) | 26.9 ± 1.1 | 28.6 ± 1.1 | 30.3 ± 1.1 | 0.10 |
| Gestational Age at Delivery (wks) | 27.3 ± 0.9 | 29.8 ± 1.0 | 37.0 ± 0.9 | <0.0001 |
| Enrollment to Delivery Interval (days) | 2.1 ± 5.6 | 8.4 ± 6.3 | 46.9 ± 5.6 | <0.0001 |
| Delivery 7 days | 10(91%) | 6(55%) | 0 | <0.001 |

Data expressed as mean standard deviation. Analysis by ANOVA for continuous data and Chi-square for categorical data. Abbreviations: PMD, premature delivery <35 weeks; IUI, intrauterine infection; PML, premature labor without delivery.

TABLE 1B

Screening Results.

| Characteristic | Group | | |
|---|---|---|---|
| | GROUP 1 PMD with IUI (n = 11) | GROUP 2 PMD without IUI (n = 11) | GROUP 3 PML with subsequent term delivery (n = 11) p valueL GROUPS 3 VS 1 |
| Bacterial culture positive | 4/11 | 0/11 | 0/11 p < 0.01 |
| IL-6 positive | 7/11 | 0/11 | 0/11 p < 0.01 |
| Diagnostic protein profiles | 11/11 | 2/11* | 0/11 p < 0.01 |

*The two positive samples in this pool represent subclinical infection since the AF of the two subjects demonstrated low levels of bacteria, positive by PCR procedures. This indicates that protein profiling can be used to identify subclinical intraamniotic infection.

In the foregoing tables, data are expressed as mean standard deviation. Analysis by ANOVA for continuous data and Chi-square for categorical data. Abbreviations: PMD, premature delivery <35 weeks; IUI, intrauterine infection; PML, premature labor without delivery.

TABLE 1C

Fisher's test significance values for screening test results.

Fisher's Exact: PMD with IUI vs PML p < 0.05 (one-sided)

| Class | Bacterial Culture | | |
|---|---|---|---|
| | Positive | Negative | Total |
| PMD with IUI | 4 | 7 | 11 |
| PML, term delivery | 0 | 11 | 11 |
| Total | 4 | 18 | 22 |

Fisher's Exact: PMD with IUI vs PML p < 0.01 (one-sided)

| Class | IL-6 Status | | |
|---|---|---|---|
| | Positive | Negative | Total |
| PMD with IUI | 7 | 4 | 11 |
| PML, term delivery | 0 | 11 | 11 |
| Total | 7 | 15 | 22 |

Fisher's Exact: PMD with IUI vs PML p < 0.005 (one-sided)

| Class | Diagnostic Protein Profile | | |
|---|---|---|---|
| | Positive | Negative | Total |
| PMD with IUI | 11 | 0 | 11 |
| PML, term delivery | 0 | 11 | 11 |
| Total | 11 | 11 | 22 |

Fisher's Exact: PMD with IUI vs PMD without IUI p < 0.005 (one-sided)

| Class | Diagnostic Protein Profile | | |
|---|---|---|---|
| | Positive | Negative | Total |
| PMD with IUI | 11 | 0 | 11 |
| PMD without IUI | 2 | 9 | 11 |
| Total | 13 | 9 | 22 |

TABLE 1C-continued

Fisher's test significance values for screening test results.

Fisher's Exact: PMD without IUI vs PML p n.s.

| Class | Diagnostic Protein Profile | | |
|---|---|---|---|
| | Positive | Negative | Total |
| PMD without IUI | 2 | 9 | 11 |
| PML, term delivery | 0 | 11 | 11 |
| Total | 2 | 20 | 22 |

Proteomic Analysis of Amniotic Fluid

1-Dimensional (1-D) Gel Electrophoresis

100 μg of amniotic fluid after reduction with iodoacetamide was loaded on a 15% SDS-PAGE gel. Electrophoresis was conducted at 80V to separate the proteins in the sample. After electrophoresis the gel was stained with Coomasie blue R-250 and images were collected using BIO-RAD GS800™ densitometer and PDQUEST™ software. Individual bands were cut from the gel, destained and digested in-gel with trypsin for 24–48 hrs at 37° C. The peptides were extracted with 0.1% TFA and dried in a speedvac. The extract was dissolved in 0.1% TFA and purified using ZIP TIP™ c18 pipette tips from MILLIPORE™. (Marvin L., et al. Identification of proteins from one-dimensional sodium dodecyl sulfate-polyacrylamide gel electrophoresis using electrospray quadrupole-time-of-flight tandem mass spectrometry. Rapid Commun Mass Spectrom. 14(14):1287–92, 2000).

2-Dimensional (2-D) Gel Electrophoresis

Amniotic fluid (400–2000 μg) with or without removal of albumin was dissolved in IEF buffer and rehydrated on to a 24 cm IPG strip (pH 3–10) for 12 h at room temperature. After rehydration, the IPG strip was subjected to 1-dimension electrophoresis at 70~90 kVhrs. The IPG strip was then equilibrated with DTT equilibration buffer I and IAA equilibration buffer II for 15 minutes sequentially, before second dimension SDS-PAGE analysis. The IPG strip was then loaded on to a 4~20% SDS-PAGE gel and electrophoresis conducted at 120 V for 12 hrs to resolve proteins in the second dimension. The gel was stained with Coomassie Blue R-250 and imaged using BIO-RAD GS800™ densitometer and PDQUEST™ software. Individual spots were cut from the gel, destained and digested in-gel with trypsin for 24–48 hrs at 37° C. The peptides were extracted with 0.1% TFA and purified using ZIP TIP™$_{c18}$ pipette tips from MILLIPORE™ (2-D Proteome analysis protocols: Methods in Molecular Biology: 112, 1999).

HPLC Fractionation

Human amniotic fluid samples after removal of albumin and IgG (1–15 mg protein) were dissolved in 20 mM Tris-HCl, pH 7.5. Anion-exchange chromatography was performed using TSK gel DEAE-5PW column on a Waters 1525 HPLC equipped with an auto sampler and a UV absorbance detector. A linear salt elution gradient was used to fractionate the proteins. Fractions were collected at one minute intervals. Fractions were pooled, digested with trypsin and peptide mixtures were analyzed using the mass spectrometer (Q-Tof-2).

Mass Spectrometry Analysis (1) Q-Tof-2

Samples after in-gel digestion were analyzed on a Micromass Q-Tof-2 mass spectrometer connected to a Micromass CapLC. The Q-Tof-2 was equipped with a regular Z-spray or nanospray source and connected to a Integrafrit C18 75 um ID×15 cm fused silica capillary column. The instrument was controlled by, and data were acquired on, a Compaq workstation with Windows NT and MassLynx 3.5 software. The Q-Tof-2 was calibrated using Glu1 Fibrinopeptide B by direct infusion or injection into the CapLC. A MS/MSMS survey method was used to acquire MS/MSMS spectra. Masses 400 to 1500 were scanned for MS survey and masses 50 to 1900 for MSMS. Primary data analysis was performed on a PC with Windows 2000 and SEQUEST (version 1.3) and/or LUTEFISK. Peak lists were generated, using the built-in automatic functions for peak-picking and applying centroid-fitting to each peak.

(2) LCQ-MS

Protein spots from dried Coomassie blue stained gels were excised and rehydrated/washed for 30 min. in 0.5 ml of 20 mM ammonium bicarbonate, 50% acetonitrile solution. The gel regions were then dried by vacuum centrifugation and digested insitu by rehydrating in 20 nM sequencing grade modified trypsin (ProMega, Madison, Wis., USA) using the method of Courchesne and Patterson, Identification of proteins by matrix-assisted laser desorption/ionization masses, *Methods Mol. Biol.* 112:487–511 (1999). Tryptic digests were then concentrated by vacuum centrifugation, separated by reverse phase chromatography, and peptides analyzed by a model LCQ™ ion trap mass spectrometer (ThermoFinnigan, San Jose, Calif.). Samples were separated with ZORBAX™ C-18 0.5 mm×150 mm microbore column using a 10 µL min$^{-1}$ flow rate and a gradient of 0 to 40% B (75% Acetonitrile in water) over one hour with an 1100 CAPILLARY LC SYSTEM™ (Agilent Technologies, Foster City, CA.). Peptides were introduced directly into the standard ThermoFinnigan electrospray source. MS/MS spectra were acquired in an automated fashion using standard LCQ™ software and then analyzed further using SEQUEST™ (ThermoFinnigan). For further details see, Courchesne, P. L. and Patterson, S. D., supra.

Data Analysis (1) Sequest and DTASelect

Automated analysis of tandem mass spectra (MS/MS) was performed using SEQUEST™ software (ThermoFinnigan) as described by Yates et al., *Methods Mol. Biol.* 112:553–69 (1999). SEQUEST™ matches uninterrupted tandem mass spectra to database peptide sequences. Searches were run with the default parameters using a combined indexed non-redundant database of protein sequences obtained from the Protein Information Resource (release date) and SwissProt™ (release date). The database was constructed using the Xcalibur Database Manager™ (ThermoFinnigan). S-Carboxyamidated cysteine was the only considered modification.

SEQUEST™ results were further analyzed using DTASELECT™ (The Scripps Research Institute, Tabb, 2002). DTASELECT™ organizes and filters SEQUEST™ identifications. The default parameters were used except as follows: 1) any database matches including the string "keratin" in the protein description were excluded and 2) spectra from the LCQ™ mass spectrometer were filtered with a cross correlation score cut-off of 2.4 for the doubly charged ions. Each spectra and proposed sequence pair selected by DTA-SELECT™ were visually inspected and the final results were input into a spreadsheet (MICROSOFT EXCEL™) or a database (MICROSOFT ACCESS™) for management.

For further details, see also: Tabb D L, et al., DTASelect and Contrast: Tools for Assembling and Comparing Protein Identifications from Shotgun Proteomics. *J Proteome Res.* 1:21–26 (2002).

(2) Lutefisk

Automated de novo sequencing of all spectra was performed using a computer program, Lutefisk 1900™ v1.2.5 (Taylor J A, Johnson R S. Implementation and uses of automated de novo peptide sequencing by tandem mass spectrometry. *Anal Chem* 73(11):2594–604 (2001). Lutefisk™ generates peptide sequences for spectra of which some are sufficiently detailed for homology-based sequence searches. Modifications, acrylamide, carbamidomethylation, and phosphorylation, were considered.

MALDI Detection Protocol and Parameters

MALDI mass spectrometry was performed on a custom-built time-of-flight reflector mass spectrometer (Jensen ON, et al., Direct observation of UV-crosslinked protein-nucleic acid complexes by matrix-assisted laser desorption ionization mass spectrometry. *Rapid Commun Mass Spectrom* 7(6):496–501 (1993)) equipped with a two-stage delayed extraction source. Approximately 1 µL of sample solution was mixed with 1 µL SA (Sinapinic acid in 60:40 water/acetonitrile 0.1% TFA final conc.) A 1.0 µL droplet of this analyte/matrix solution was deposited onto a matrix pre-crystallized sample probe and allowed to dry in air. Mass spectra were produced by radiating the sample with a (355 nm) Nd:YAG laser (Spectra Physics) and operating the ion source at 23 kV with a 700 ns/1.0 kV delay. Every mass spectrum was recorded as the sum of 20 consecutive spectra, each produced by a single pulse of photons. Ions from an added standard were used for mass calibration.

SELDI Analysis of Amniotic Fluid

A total of 0.5–3.0 ug protein from amniotic fluid samples was spotted on a Normal Phase NP20 (SiO$_2$ surface), Reverse Phase H4 (hydrophobic surface: C-16 (long chain aliphatic), or immobilized nickel (IMAC) SELDI PROTEINCHIP® array (Ciphergen Biosystems, Inc. Fremont, Calif.). After incubation at room temperature for 1 hour, NP1 and H4 chips were subjected to a 5 ul water wash to remove unbound proteins and interfering substances (ie buffers, salts, detergents). After air-drying for 2–3 minutes, two 0.5 ul applications of a saturated solution of sinapinic acid in 50% acetonitrile (v/v), 0.5% trifluoroacetic acid (v/v) was added and mass analysis was performed by time-of-flight mass spectrometry in a Ciphergen Protein Biology System II™ (PBS II), Issaq, J. H, et al.: The SELDI-TOF MS Approach to proteomics: Protein Profiling and Biomarker Identification. Biochem Biophys Res Commun. 5;292(3): 587–92, 2000.

EXAMPLE 2

Identification of Proteins and Polypeptides Expressed in the Amniotic Fluid

Using the materials and methods described in Example 1, proteins and polypeptides expressed in normal and infected amniotic fluid were identified. Human and primate amniotic fluid samples (pooled and individual) were subjected to protein separation techniques (1-D, 2-D and HPLC fractionation) as described in Example 1. The separated proteins (gel bands, spots and fractions) were digested with trypsin to generate peptide pools. The peptide pools were analyzed using tandem MS to decipher their amino acid sequence and composition.

Five thousand MS spectra were selected using spectral verification programs. These spectral files were analyzed using de novo sequencing programs (LUTEFISK™, PEAKS™) to generate the amino acid sequence corresponding to each peptide. The de novo sequences generated from the peptide pool were used to search protein and DNA databases as described in Example 1.

Using homology maps and sequence verification, expression of a variety of proteins was discovered in the amniotic fluid. The detected proteins were analyzed for potential function based on known structural similarities (sequence homology maps). Proteins belonging to important functional classes involved in a wide range of diseases were discovered. Proteins and polypeptides discovered for the first time in the human amniotic fluid are listed in the following Table 2 under these potential functional categories.

Proteins shown to be differentially expressed by immunoassays also, and proteins more abundantly or uniquely represented in the infected amniotic fluid are separately marked. In this context, relative abundance is defined as the amount of the peptides representing a certain polypeptide or protein in a test sample, relative to a reference sample. Accordingly, a protein is more abundantly represented in infected amniotic fluid if more peptides derived from the same protein are present in infected amniotic fluid than in a non-infected reference sample of amniotic fluid.

Table 3 lists proteins and polypeptides previously known to be present in amniotic fluid, the presence of which was reaffirmed by the present assays. Proteins which are known markers for infection related events are separately marked.

TABLE 2

Proteins and polypeptides discovered for the first time in the human amniotic fluid

| GenBank Acc. No | Protein ID | Protein Name |
|---|---|---|
| Immune response related genes | | |
| U12026 | CAPG_HUMAN | Macrophage capping protein# |
| X83006 | NGAL_HUMAN | Neutrophil gelatinase-associated lipocalin# |
| M19507 | PERM_HUMAN | Myeloperoxidase precursor# |
| M22300 | PLSL_HUMAN | L-plastin (Lymphocyte cytosolic protein 1)* |
| NM001700 | AZU1_HUMAN | Azurocidin# |
| Z38026 | FA39_HUMAN | Antibacterial protein FALL-39 precursor# |
| AF159456 | Q9UKJ4 | Gp-340 variant protein |
| AL355392 | Q9H4V6 | Novel protein similar to mouse von Ebner salivary gland protein, isoform 2 (SEQ ID NO:12) |
| M93056 | ILEU_HUMAN | Leukocyte elastase inhibitor# |
| Y00278 | S108_HUMAN | Calgranulin A*# |
| X06233 | S109_HUMAN | Calgranulin B |
| Structural proteins | | |
| D00682 | COF1_HUMAN | Cofilin, non-muscle isoform |
| M69066 | MOES_HUMAN | Moesin (Membrane-organizing extension spike protein) |
| J03191 | PRO1_HUMAN | Profilin I*# |
| D44497 | CO1A_HUMAN | Coronin-like protein p57 (Coronin 1A) |
| D00017 | ANX2_HUMAN | Annexin II (Lipocortin II) |
| M15801 | FINC_HUMAN | Fibronectin precursor |
| M17783 | GDN_HUMAN | Glia derived nexin precursor# |

TABLE 2-continued

Proteins and polypeptides discovered for the first time in the human amniotic fluid

| GenBank Acc. No | Protein ID | Protein Name |
|---|---|---|
| Proteases and protease inhibitors | | |
| M21642 | ANT3_HUMAN | Antithrombin-III precursor |
| S66896 | SCC1_HUMAN | Squamous cell carcinoma antigen 1 |
| U19576 | SCC2_HUMAN | Squamous cell carcinoma antigen 2 |
| AB006423 | SPI2_HUMAN | Serpin I2 precursor# |
| X05978 | CYTA_HUMAN | Cystatin A (Stefin A) (Cystatin AS)# |
| U46692 | CYTB_HUMAN | Cystatin B (Liver thiol proteinase inhibitor) |
| X05607 | CYTC_HUMAN | Cystatin C precursor |
| Transporters and binding proteins | | |
| Y00856 | IBP1_HUMAN | Insulin-like growth factor binding protein 1-Proteolytic fragment (only)* |
| L10641 | VTDB_HUMAN | Vitamin D-binding protein precursor |
| J00098 | APA1_HUMAN | Apolipoprotein A-I precursor (Apo-AI) |
| X57348 | 143S_HUMAN | 14-3-3 protein sigma (Stratifin) |
| M86400 | 143Z_HUMAN | 14-3-3 protein zeta/delta |
| X04412 | GELS_HUMAN | Gelsolin precursor, plasma |
| X53961 | TRFL_HUMAN | Lactotransferrin precursor (Lactoferrin) |
| Enzymes and other molecules | | |
| V00572 | PGK1_HUMAN | Phosphoglycerate kinase 1 |
| J04173 | PMG1_HUMAN | Phosphoglycerate mutase 1 |
| X67688 | TKT_HUMAN | Transketolase |

*Proteins shown to be differentially expressed by immunoassays also.
Peptides representing these proteins are more abundantly or uniquely detected in the infected amniotic fluid.

TABLE 3

Proteins and polypeptides, previously known to be present in the amniotic fluid, identified using de novo sequencing.

| GenBank Acc. No | Protein ID | Protein Name |
|---|---|---|
| K02765 | CO3_HUMAN | Complement C3 precursor* |
| J00241 | KAC_HUMAN | Ig kappa chain C region |
| J00253 | LAC_HUMAN | Ig lambda chain C regions |
| J00228 | GC1_HUMAN | Ig gamma-1 chain C region |
| X57127 | H2BF_HUMAN | Histone H2B.f* |
| X00038 | H4_HUMAN | Histone H4* |
| J00153 | HBA_HUMAN | Hemoglobin alpha chain |
| U01317 | HBB_HUMAN | Hemoglobin beta chain |
| U01317 | HBD_HUMAN | Hemoglobin delta chain |
| M91036 | HBG_HUMAN | Hemoglobin gamma-A and amma-G chains |
| Z83742 | H2AC_HUMAN | Histone H2A |
| M22919 | MLEN_HUMAN | Myosin light chain alkali, non-muscle isoform |
| J05070 | MM09_HUMAN | type IV collagenase precursor* |
| V00496 | A1AT_HUMAN | Alpha-1-antitrypsin precursor* |
| K01500 | AACT_HUMAN | Alpha-1-antichymotrypsin precursor* |
| M12530 | TRFE_HUMAN | Serotransferrin precursor |
| M11714 | TTHY_HUMAN | Transthyretin precursor (Prealbumin) |
| M13699 | CERU_HUMAN | Ceruloplasmin precursor* |
| X02544 | A1AH_HUMAN | Alpha-1-acid glycoprotein 2 precursor* |
| X06675 | A1AG_HUMAN | Alpha-1-acid glycoprotein 1 precursor* |
| M12523 | ALBU_HUMAN | Serum albumin precursor |
| J00098 | APA1_HUMAN | Apolipoprotein A-I precursor (Apo-AI) |

*Known markers for infection related events.

Diagnostic Markers for Intrauterine Conditions:

In view of their known biological functions, several proteins listed in the foregoing tables are promising candidates for detecting and monitoring intrauterine conditions. A few examples of such conditions and the corresponding protein markers are discussed below in greater detail.

Actin-modulating and Related Proteins as Markers of Developmental Defects:

Moesin (Membrane-organizing extension spike protein), listed among the structural proteins in Table 2, is known to be responsible for linking transmembrane proteins to the actin cytoskeleton and implicated in various cell signaling pathways (Speck O, et al.: Moesin functions antagonistically to the Rho pathway to maintain epithelial integrity. *Nature* 2;421(6918):83–7, 2003). It was shown that Rho-family GTPases and their effectors to modulate the activities of actin modifying molecules such as Cofilin and Profilin (also listed as a structural protein in Table 2), resulting in cytoskeletal changes associated with growth cone extension or retraction (Tang B L. Inhibitors of neuronal regeneration: mediators and signaling mechanisms. Neurochem Int, 42(3): 189–203, 2003). Coronin-like protein p57 (yet another structural protein listed in Table 2) is also involved in actin cross-linking and capping (Weitzdoerfer R et al.: Reduction of actin-related protein complex 2/3 in fetal Down syndrome. Biochem Biophys res Commun. 293:836, 2002) and are dysregulated in known developmental defects. Gelsolin (see, the Gelsolin precursor listed an a transporter/binding protein in Table 2), another actin-modulating protein is also known to be developmentally regulated and important in organ systems (Arai M, Kwiatkowski D J. Differential developmentally regulated expression of gelsolin family members in the mouse. Dev Dyn, 215, 297, 1999). 14-3-3 proteins are also known epithelial markers which participate in signal transduction and differentiation pathways and are essential for normal development of brain and other vital organs (Wu C, Muslin AJ. Role of 14-3-3 proteins in early Xenopus development. Mech Dev, 119, 45, 2002).

Accordingly, the listed actin-modulating proteins and other related molecules with important roles during development, that were identified for the first time in human amniotic fluid, could be used to detect developmental defects of various organ systems such as, central nervous system, cardiovascular system and other musculoskeletal deformities, which can, for example, result from chromosomal aneuploides. This is particularly true for Profiling I, which has been shown to be differentially expressed in infected amniotic fluid, and the differential expression of which has been confirmed by immunoassay.

Markers of Infection and Immune-response Related Disorders:

The present detection of macrophage capping protein, leukocyte elastase, neutrophil gelatenase-associated lipocalicn, myleoperoxidase, L-plastin (lymphocyte cytosolic protein) and calgranulins (see the list of immune response related genes in Table 2) infected amniotic fluid is the first demonstration of the presence and regulation of these proteins in intraamniotic infection. Several of these proteins are known responders of immune cells in response to infection, inflammation and stress. Macrophage capping protein (MCP) is a Ca(2+)-sensitive protein which modulates actin filaments and involved in inflammatory process (Dabiri G A, Molecular cloning of human macrophage capping protein cDNA. A unique member of the gelsolin/villin family expressed primarily in macrophages J Biol Chem 15;267 (23):16545–52, 1992). Similarly, Calgranulins are calcium binding proteins known to play a role in injury and wound healing (Thorey IS. et al. The Ca2+-binding proteins S100A8 and S100A9 are encoded by novel injury-regulated genes. J Biol Chem 21;276(38):35818–25, 2001). Leukocyte elastase and neutrophil gelatinase-associated lipocalcin (NGAL) are involved in bacteriostatic and baceterolysis mechanisms (Goetz D H. et al. The neutrophil lipocalin NGAL is a bacteriostatic agent that interferes with siderophore-mediated iron acquisition.: Mol Cell 10(5):1033–43, 2002).

In addition to the above immunomodulators we also discovered, for the first time, two antibacterial proteins Fall-39 and azurocidin in the infected amniotic fluid. Antibacterial protein Fall-39 (LL-37) binds to bacterial lipopolysaccharides (1 ps), and is expressed in bone marrow, testis and neutrophils. Fall-39 stimulates the degranulation of mast cells, and is a potent chemotactic factor for mast cells. Besides its antibacterial activities, Fall-39 may have the potential to recruit mast cells to inflammation foci. In the presence of the basal medium E, synthetic FALL-39 was highly active against *Escherichia coli* D21 and Bacillus megaterium Bm11. A protective role for Fall 39 has been proposed, when the integrity of the skin barrier is damaged, participating in the first line of defense, and preventing local infection and systemic invasion of microbes (Agerberth B, et al.: FALL-39, a putative human peptide antibiotic, is cysteine-free and expressed in bone marrow and testis. Proc Natl Acad Sci U S A, 3;92(1):195–9, 1995).

Azurocidin (CAP37) is a cationic antimicrobial protein isolated from human neutrophils and has important implications in host defense and inflammation. It is released during inflammation and regulates monocyte/macrophage functions, such as chemotaxis, increased survival, and differentiation (Pereira H A. CAP37, a neutrophil-derived multifunctional inflammatory mediator. J Leukoc Biol ;57 (6):805–12, 1995).

Proteases and protease inhibitors play a key role in protein regulation and thus control several key physiological mechanisms. We have identified the expression of Serpin family of proteases (Serpin, squamous cell carcinoma antigen 1 & 2, glia derived nexin) for the first time in human amniotic fluid, including intraamniotic infection. The serpin superfamily of serine proteinase inhibitors has a central role in controlling proteinases in many biological pathways and implicated in conformational diseases, such as the amyloidoses, the prion encephalopathies and Huntington and Alzheimer disease (Lomas D A, Carrell R W, Serpinopathies and the conformational dementias. Nat Rev Genet; 3:759, 2002).

Additionally, in intraamniotic infection we identified the expression of Cystatins, well known proteinase inhibitors involved in immunomodulation (Vray B, Hartmann S, Hoebeke J. Immunomodulatory properties of cystatins. Cell Mol Life Sci;59(9): 1503–12,2002).

The listed proteins are promising markers of infection and/or immune-response related disorders.

It is noteworthy that peptides representing macrophage capping protein, neutrophil gelatinase-associated lipocalin, myeloperoxidase precursor, L-plastin, azurocidin, antibacterial protein Fall-39, calgranulin A, profilin I, glia-derived nexin, serpin I2, and cystatin A were more abundantly or uniquely detected in infected amniotic fluid relative to normal amniotic fluid, and/or showed differential expression in immunoassays. Accordingly, these proteins are particularly important as markers of intra-amniotic infection and/or immune-response related disorders.

Other Disease(Infection) Specific Proteins Detected in Human Amniotic Fluid

Gp-340 variant protein listed in Table 2, which has been detected in human infected amniotic fluid, is a scavenger receptor previously identified in lung. This protein is known to bind to bacteria (streptococcus and variants ) The detection of this protein in infected amniotic fluid complements the sensitive proteomic approach of the present invention to identify biomarkers for IAI. Thus, Gp-340 variant protein identified in the infected amniotic fluid lends itself for the detection of neonatal sepsis).

IGFBP-1 (Proteolytic Fragment)

As shown in Table 2, IGFBP-1 has been shown to be differentially expressed in infected amniotic fluid. The insulin-like growth factor (IGF) systems is critically involved in fetal and placental growth and modulates steroid hormone actions in the endometrium through autocrine/paracrine mechanisms. IGF-I and IGF-II stimulated proliferation and differentiation, and maintain differentiated cell functions in several cell types in vitro. Endometrial stromal cells produce IGF-I and IGF-II as well as the high affinity IGF-binding proteins (IGFBPs). The mRNA of six high affinity IGFBPs, which can modulate IGF actions, are expressed in human endometrium. The most abundant IGFBP in human endometrium is IGFBP-1, which is secreted by predecidualized/decidualized endometrial stromal cells in late secretory phase and during pregnancy. This has implications for clinical obstetrics and gynecology, where there is evidence for a pathophysiological role for IGFBP-1 in pre-eclampsia, intrauterine growth restriction, polycystic ovarian syndrome and trophoblast and endometrial neoplasms.

The presence and regulation of an IGFBP-1 proteolytic fragment in human amniotic fluid and maternal serum opens a new way for monitoring intrauterine and maternal conditions associated with pregnancy.

For further details see, also Example 12 below.

EXAMPLE 3

Figure 1B:
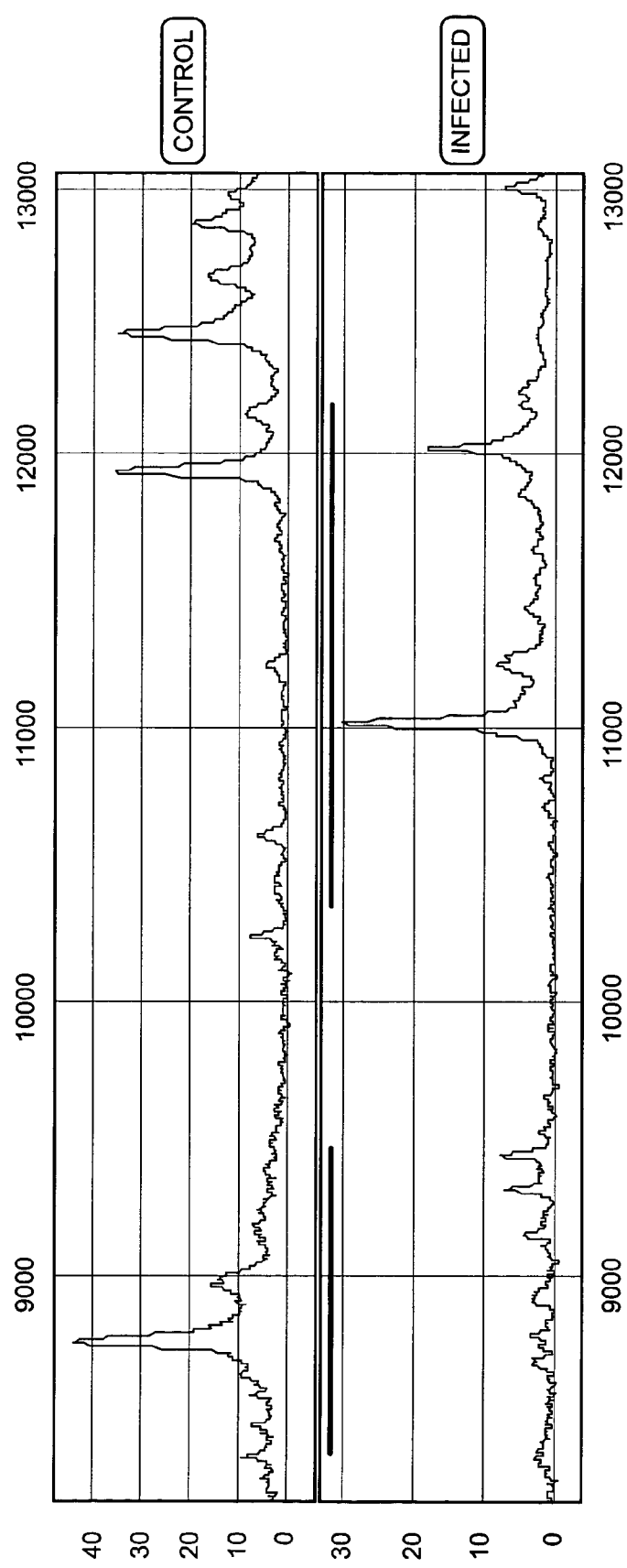
Figure 1C:
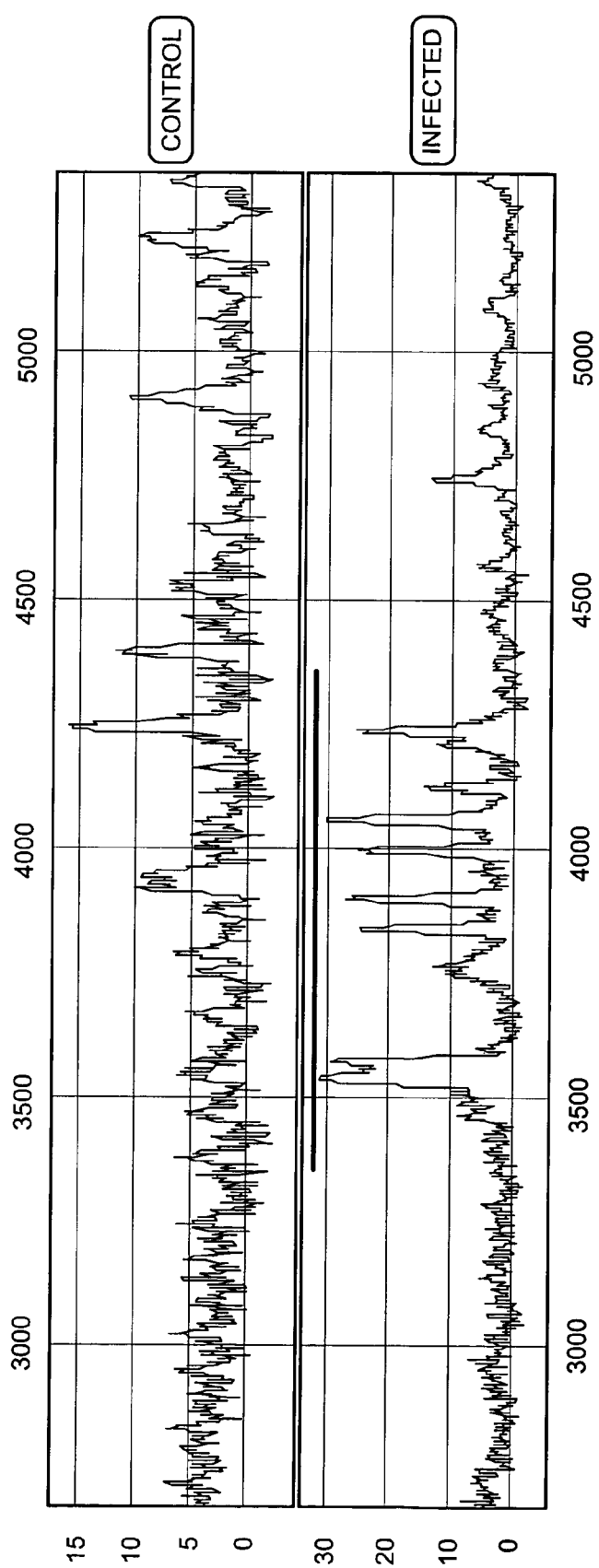

Protein Expression Profiles of Primate Amniotic Fluid Following Intrauterine Infection Protein expression profiles of primate amniotic fluid following intrauterine infection, compared with the corresponding normal expression profiles, are shown in FIGS. 1A–C.

As illustrated in FIGS. 1A–C, the global protein expression profiles of control and infected amniotic fluid are distinct. A detailed spectra of amniotic fluid profiles in a smaller mass range (FIGS. 1B and 1C), shows distinct and characteristic differences between the protein expression profiles of control and infected samples approximately in the 3–5 KDa and 10–12 KDa range. This illustrates global regulation of protein expression in response to intrauterine infection and the ability to detect a unique expression signature diagnostic of intrauterine infection.

EXAMPLE 4

Early Detection of Diagnostic Pattern/Profile of Infection in the Primate Amniotic Fluid FIG. 2 shows the time course analyses of the primate amniotic fluid in response to infection (GBS). Amniotic fluid was collected before the inoculation of bacteria and serially after infection and subjected to SELDI-TOF analysis as described in Example 1. FIG. 2A shows the protein expression profile before infection, FIG. 2B 12 hours after infection, and FIG. 2C 36 hours after infection.

As shown in FIG. 2C, one of the diagnostic peaks (10–11 KDa) of intrauterine infections clearly reaches high levels of expression within 36 hours of acute infection. This demonstrates that diagnostic protein profiles can be used for monitoring the disease state and response to treatment.

EXAMPLE 5

Figure 3A:
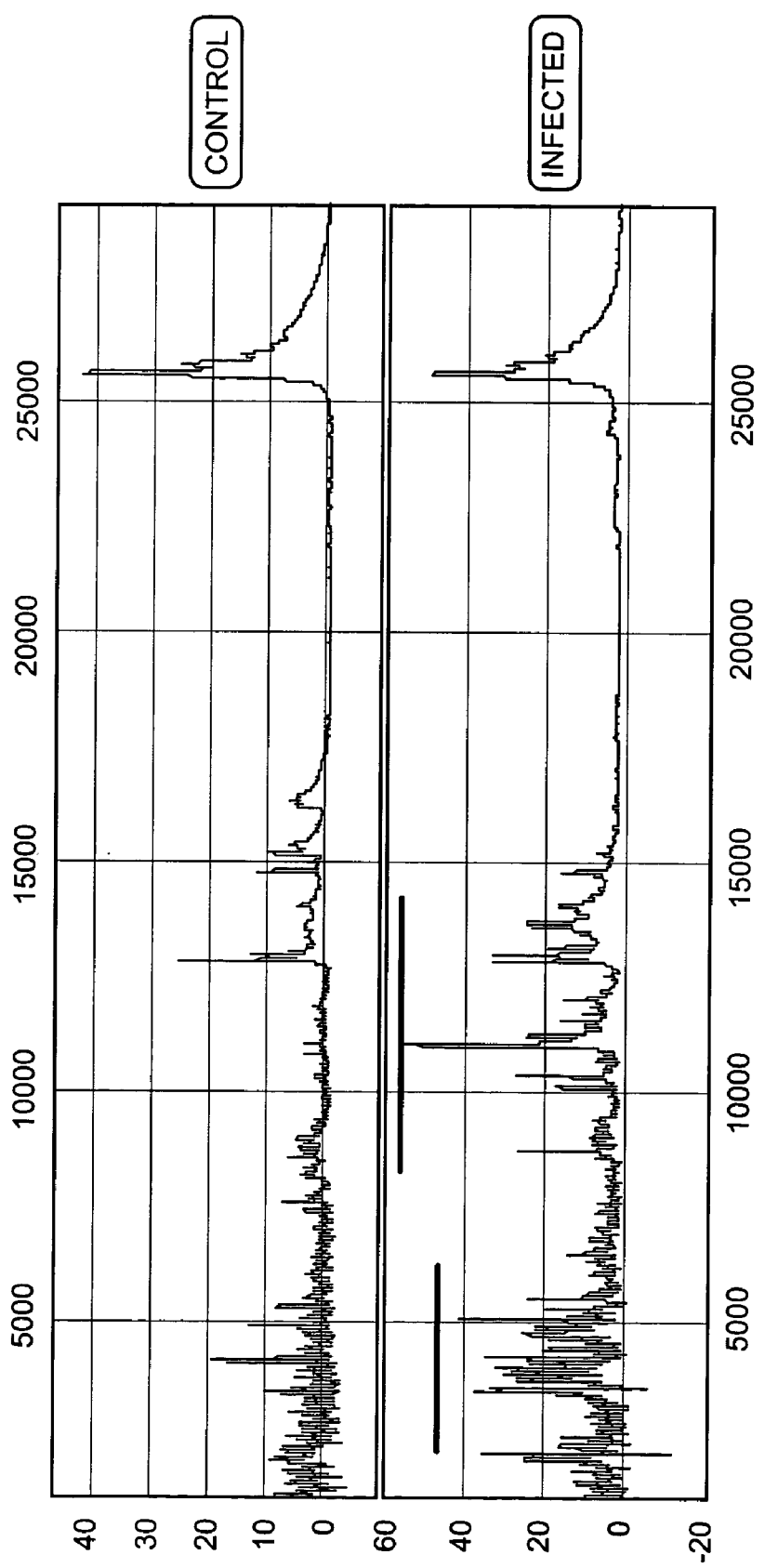
FIGS. 3A–C. Infection-induced differential protein expression in the human amniotic fluid. SELDI-TOF analysis of amniotic fluid extracts bound to chemically defined Normal Phase chip arrays. A). Whole spectrum collected at 235 laser intensity showing the differences in the peak intensities. B) Detailed spectrum showing the differences in the 10 to 12 KDa region between control and infected. C) Detailed spectrum showing the differences in the 3–5 KDa region between control and infected. D) Peak intensity based clusters that differentiates between control and infected.
Figure 3B:
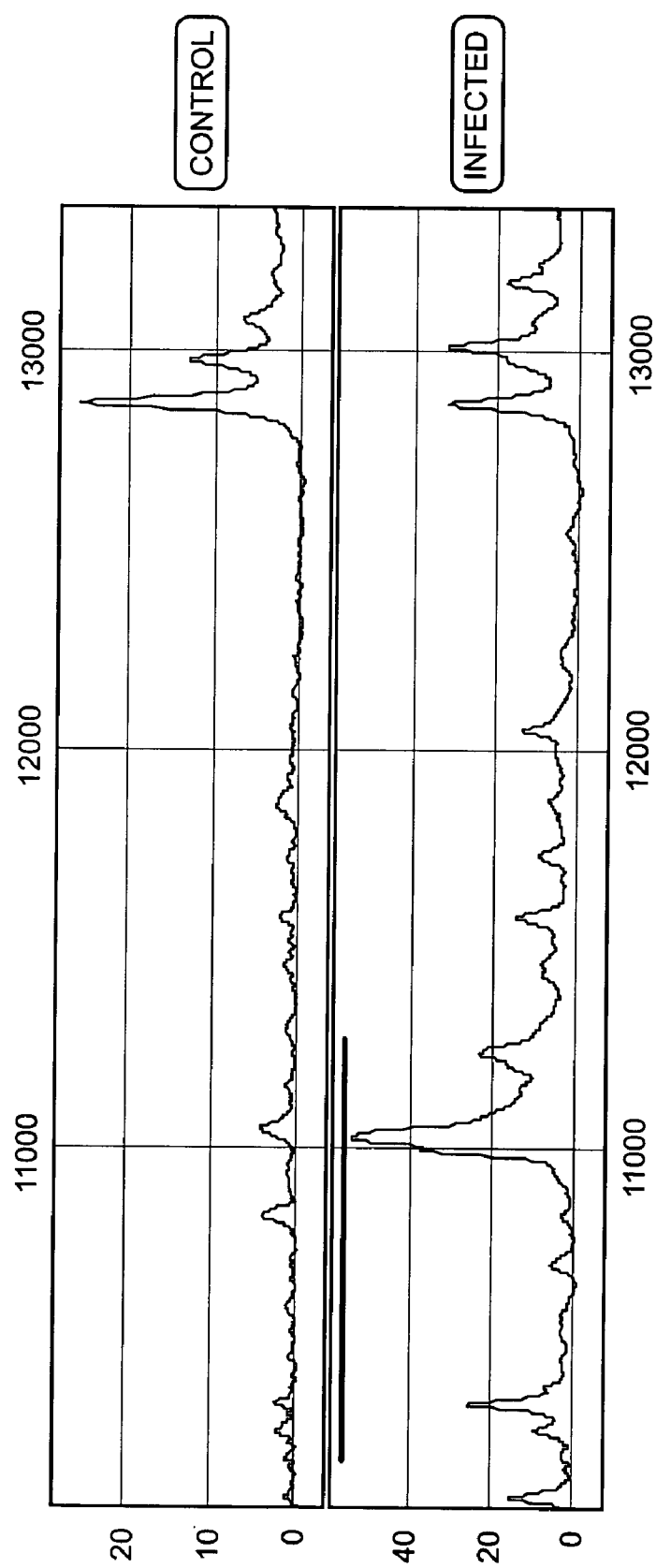

Protein Expression Profiles of Human Amniotic Fluid Following Intrauterine Infection FIG. 3 shows the results of SELDI-TOF analysis of amniotic fluid extracts bound to chemically defined normal phase chip arrays. FIG. 3A shows the whole spectrum at 235 laser intensity. FIG. 3B is a detailed spectrum showing the differences between infected and control samples in the 10–12 kDa region. FIG. 3 is a detailed spectrum showing the characteristic differences between infected and control samples in the 3–5 kDa region.

Figure 3C:
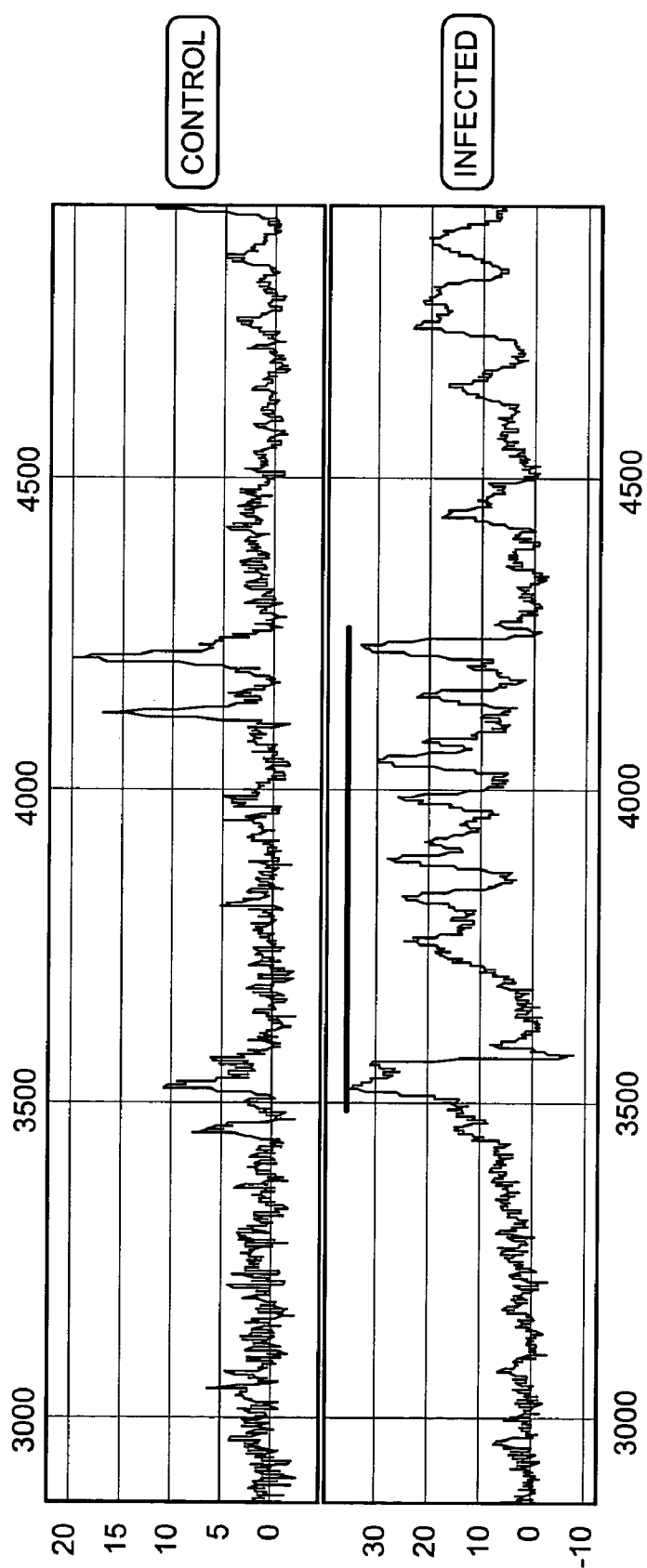

As shown in FIGS. 3A–C, the global protein expression profiles of control and infected amniotic fluid are distinct. A detailed spectra of amniotic fluid profiles in a smaller mass range (FIGS. 3B and C), shows distinct over expressed proteins (3–5 KDa and 10–12 KDa range) between control and infected samples. Analysis of protein peaks relative intensities, suggests the presence of two distinct diagnostic clusters (10–12 kDa and 3–5 kDa ranges). This illustrates global regulation of protein expression in response to intrauterine infection and the ability to detect a unique expression signature diagnostic of intrauterine infection both in human and primate models.

It is noteworthy that the diagnostic pattern of human amniotic fluid is in good agreement with the diagnostic pattern of primate amniotic fluid (Examples 3 and 4).

EXAMPLE 6

Generation of Diagnostic Profiles Using Different Mass Spectrometers

The diagnostic protein expression profile can be detected using different types of mass spectrometers. It has been examined whether different mass spectrometers produce similar diagnostic profiles. If the diagnostic profiles are substantially independent on the type of mass spectrometer, the detected differential protein expression in the amniotic fluid can provide a diagnostic signature for intrauterine infection.

Figure 4A:
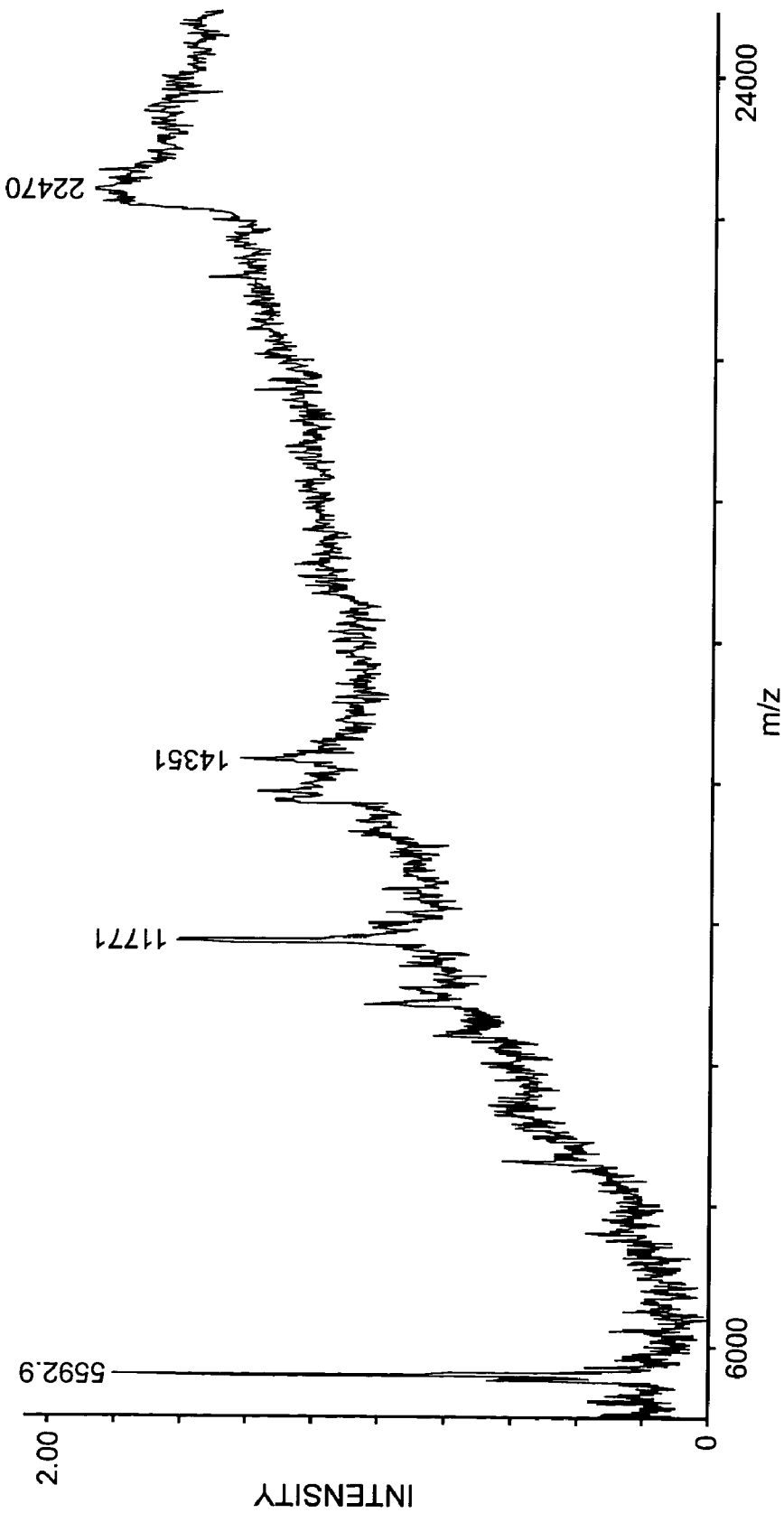
FIGS. 4A and 4B. Mass spectra acquired on a generic MALDI-TOF mass spectrometer, using amniotic fluid from human A) control, without intrauterine infection and B) sample, with intrauterine infection.
Figure 4B:
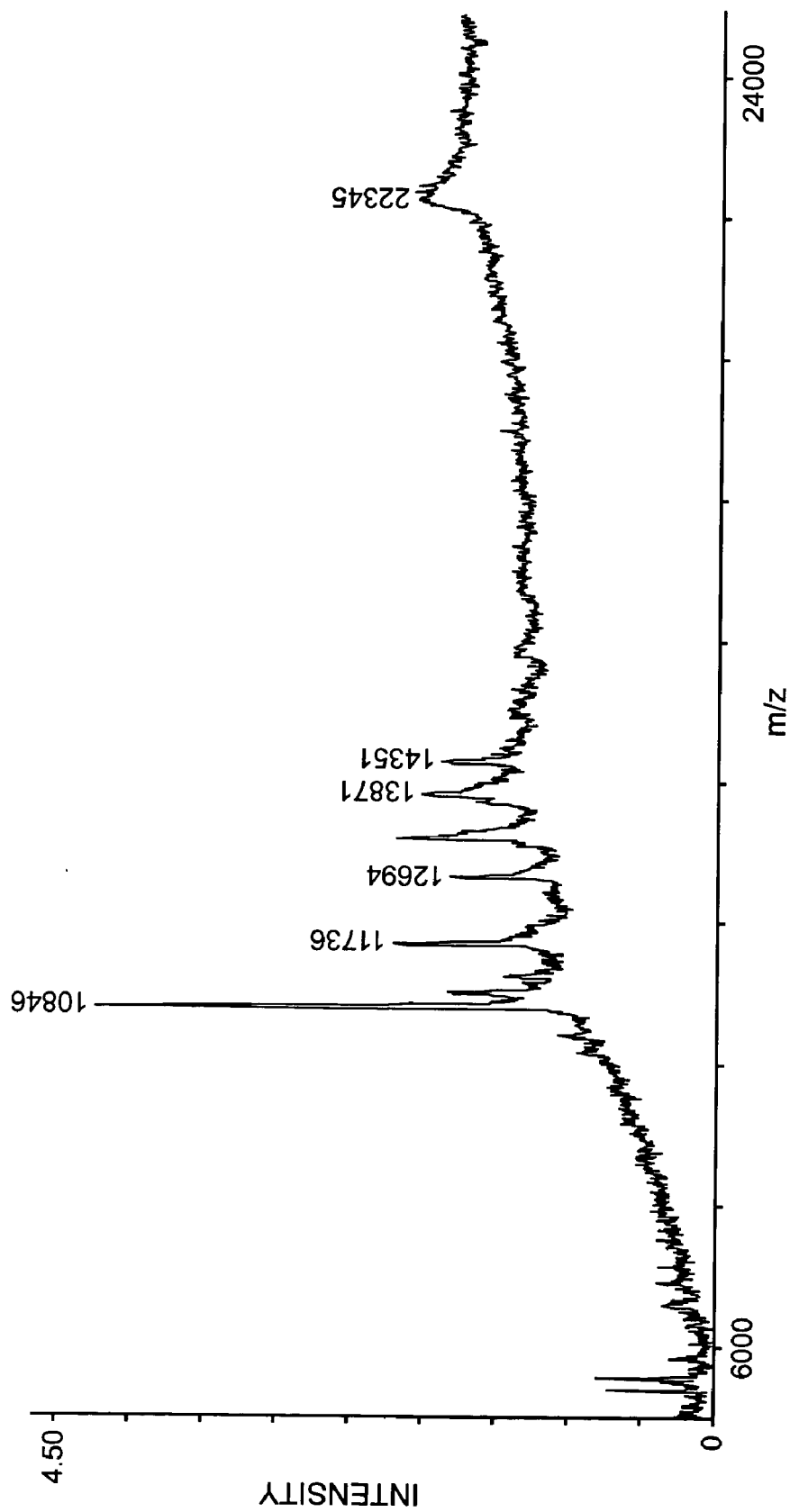

FIG. 4 shows mass spectra acquired on a generic MALDI-TOF mass spectrometer (Jensen O N, et al., Direct observation of UV-crosslinked protein-nucleic acid complexes by matrix-assisted laser desorption ionization mass spectrometry. *Rapid Commun Mass Spectrom* 7(6):496–501 (1993)) using amniotic fluid from human control (A), without intrauterine infection, and a sample (B) with intrauterine infection.

As shown in FIGS. 4A and B, the diagnostic profile of intrauterine infection in the 10–12 KDa range is detected using the alternate mass spectrometer is similar to the profile detected using the SELDI-TOF machine. This indicates that differential protein expression profiles are robust and can be detected using a wide range of current mass spectrometers.

In summary, it has been discovered that amniotic fluid proteins and polypeptides exhibit differential expression patterns diagnostic of disease state. The results presented here demonstrate that disease-specific diagnostic patterns can be detected using multiple mass spectrometry approaches. The patterns or protein expression profiles are comparable between humans and primates. The profiles can be used to monitor a time-course (infection or treatment) effect.

EXAMPLE 7

Quantification of Protein and Polypeptide Expression in Amniotic Fluid for Diagnostic and Prognostic Monitoring

SDS-PAGE:

Proteins from human amniotic fluid (AF) containing high salt was precipitated with acetone. 100 μg of amniotic fluid proteins was run on a 15% SDS-PAGE. The gel was stained with Coomassie Blue R-250. The gel image was scanned by Bio-Rad gel Scanner.

FIG. 5 shows the SDS-Coomassie Blue stained gel of A) 4 human control AF samples pooled; B) individual control AF sample; C) 4 human infected AF samples pooled; and D) individual infected AF sample.

FIG. 5 shows significant differences between the control and infected protein expression levels in the 10–15 KDa range. It has been concluded that some of the proteins and proteolytic fragments in this mass detected using the mass spectrometers are responsible for the diagnostic profiles reflective of the protein expression levels, and have diagnostic and prognostic utility.

EXAMPLE 8

Western Blot Analysis of Amniotic Fluid from Intrauterine Infection

100 μg of AF proteins were run on 4–20% SDS-PAGE at 200 V for 60 minutes and transferred to PVDF membrane at 90 mM for 75 minutes. The membrane was blocked with 5% milk PBST for 45 min at RT and incubated with 1 μg/ml primary antibody (Santa Cruz and Dako) overnight at 4 C. After wash with TBST 3 times, the membrane was incubated with secondary antibody IgG-HRP (Sigma) for 90 min at RT and visualized with ECL (Pierce).

The results are shown in FIG. 6: A) Control AF sample (pooled); B) Infected AF sample (pooled). FIG. 6 shows that IGFBP1 (11 KDa), profilin and ceruloplasmin (130 KDa) are expressed at a higher level in infected AF compared to non-infected AF. L-Plastin levels were lower in the infected sample compared to control AF sample. These proteins were also identified from the human infected samples using MS approaches (de novo sequencing) and are listed in Example 2 above.

EXAMPLE 9

Immunoprecipitation Analysis of Amniotic Fluid from Intrauterine Infection

Two micrograms of primary antibody was mixed with 600 μg of AF protein and incubated at 4° C. overnight. 15 μl of protein G Sepharose beads was added and incubated on a shaker for 60 minutes at room temperature. The beads were washed with IP buffer for 6 times.

The results are shown in FIG. 7, where (A) shows the control amniotic fluid sample (pooled), and (B) shows the infected amniotic fluid sample. FIG. 7 shows that ceruloplasmin (~130 KDa) and calgranulin (~16 KDa) are expressed at a higher level in the infected amniotic fluid than control amniotic fluid.

EXAMPLE 10

Figure 8:
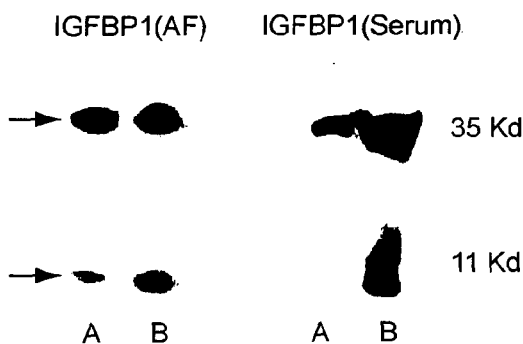
FIG. 8 shows the detection of differential protein expression in the human amniotic fluid and maternal serum. A) control sample (pooled); B) infected sample (pooled).

Detection of Differential Protein Expression in the Human Amniotic Fluid and Maternal Serum It has been examined if the differentially expressed proteins in the amniotic fluid can be used as a lead to measure similar proteins in the maternal serum. This will enable to develop rapid and non-invasive testing for diagnoses and monitoring. The results are shown in FIG. 8, where (A) is the control sample (pooled), and (B) is the infected sample (pooled). FIG. 8 shows that an IGFBP-1 smaller proteolytic fragment is consistently differentially expressed both in AF and maternal serum in response to intrauterine infection.

EXAMPLE 11

Protein Microarray Analysis of Amniotic Fluid from Intrauterine Infection

Antibodies: IGFBP-1(DSL); complement C3, Desmin, neutrophil elastase, NSE antibody (DAKO); calgranulin, ceruloplasmin, TIMP-1, plastin and profiling (Santa Cruz).

Antibody spotting: antibodies were dissolved in 40% glycerol, 60% PBS, pH 7.5 at a concentration of 100 μg/ml and were spotted on aldehyde slides using a Arrayer (Cartesian).

Following a 3 hr incubation in a humid chamber at room temperature, the slides were incubated for one hour in a solution of PBS, pH 7.5 containing 1% BSA (w/v at room temperature with gentle agitation.

Figure 9:
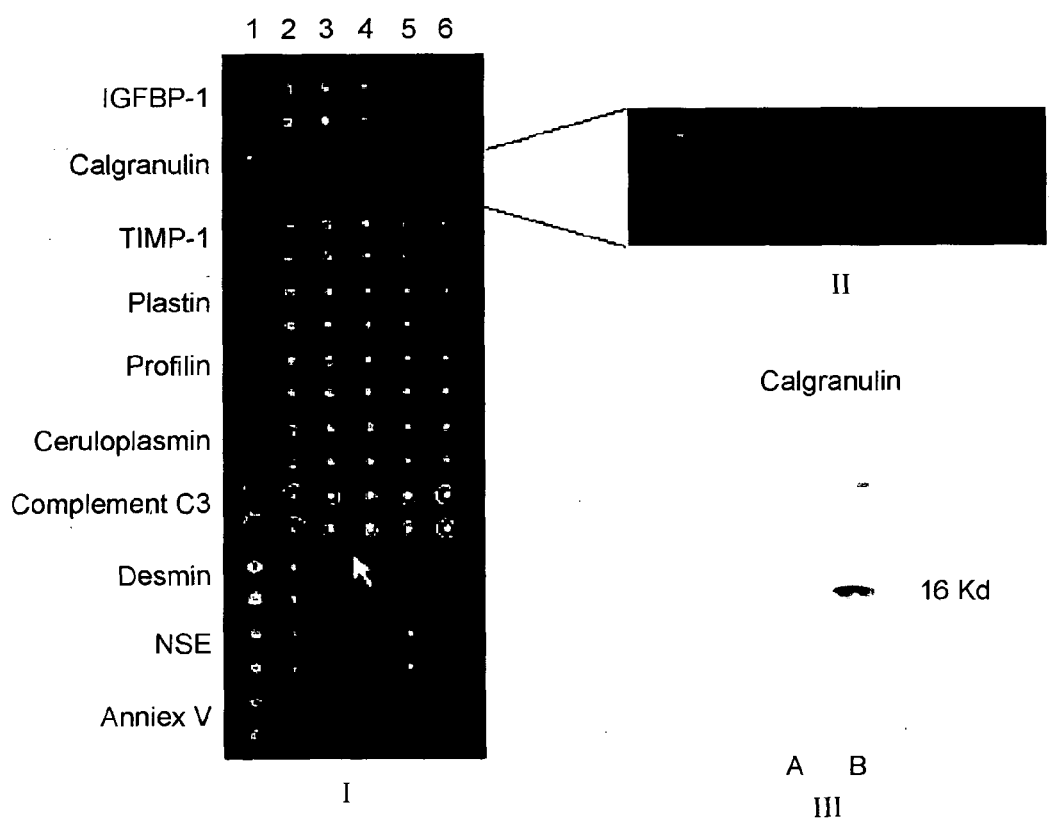
FIG. 9 shows the detection of differentially expressed proteins in maternal serum using protein arrays. 1) pseudo-color image of the protein array showing the binding of corresponding proteins with their antibodies; 2) enlarged area of the array; 3) Western blot of calgranulin IP.

Biotinylation of proteins: Biotin-NHS was dissolved in DD water at 50 mg/l. 10 ul of this solution was added into maternal serum protein solution (5 mg/ml in 10 mM PB, pH8.5) and incubated for 3 hours on a shaker. 5 ul of ethanolamine was added to stop the reaction. Biotinylated proteins were diluted in 200 ul of TNB buffer and added to antibody arrays and incubated overnight at 4 C. Following three washes in TNT buffer, streptavidin-HRP was added and incubated for 30 minutes at room temperature. Antigen-Antibody interaction was detected using Cy5-tyramide fluorescence. Slides were scanned on a PE fluorescent scanner for quantification. Images of control and infected slides were overlayed using a image analysis program to generate a pseudocolor representation for relative abundance. The results are shown in FIG. 9, which is a pseudocolor image of the protein array showing the binding of corresponding proteins with their antibodies. Green color represents infected sample, red color represents control sample. Part II is an enlarged area of the array showing that calgranulin expression (green) is higher in the infected serum sample. Part III is a western blot of calgranulin IP showing similar increased expression in the infected amniotic fluid sample.

EXAMPLE 12

Figure 13:
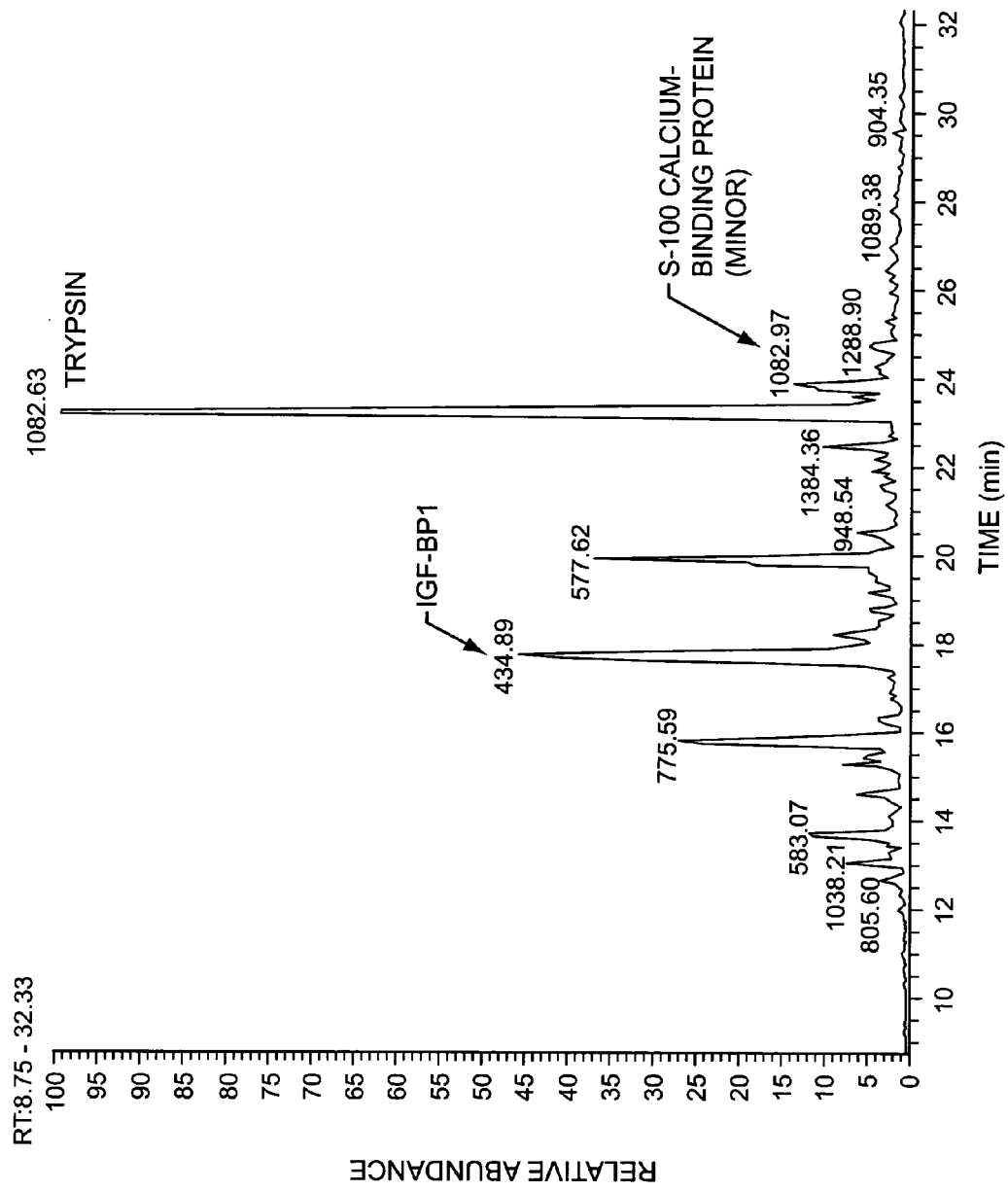
FIG. 13. LCQ-MS profile of trypsin digestion of 10.5–11 kD ID gel band from infected amniotic fluid. LCQ-MS showing parent ions representing potential proteins present in the sample.

Further Analysis of Proteins Represented in the Unique Diagnostic Signature of Infected Amniotic Fluid It has been demonstrated that the SELDI-TOF profiles of control and infected amniotic fluid show a unique signature in the mass range of 10–12 KDa (FIGS. 1, 2 and 3), representative of positively infected sample. The control and infected amniotic fluid resolved on a 1-D gel (FIG. 5) also shows bands in the mass range of 10–12 KDa that are more abundant in the pooled or independent infected amniotic fluid samples. Isolation of these 1-D gel bands and further analysis using LCQ-MS as shown in FIG. 13, identified peptides representative of IGF-BR-1 and S-100 calcium binding proteins.

Western blot analysis of control and infected amniotic fluid using an anti-IGF-BP1 antibody as shown in FIG. 8, also demonstrates the differential expression of a proteolytic fragment (~11 KDa) in infection.

Sequencing of the amniotic fluid polypeptides also identified the presence of IGF-BP1 and calgranulins in the infected amniotic fluid (Table 3).

The sequence of the identified novel proteolytic fragment of IGFBP-1 is shown in FIG. 12 (SEQ ID No.: 1). In the Figure, the peptide sequences found in samples "0426seq_HI_12" and "0425seq_HI-113" following 1-D gel electrophoresis, trypsin digestion and MS/MS analysis of infected amniotic fluid are shown in lower case (SEQ ID Nos: 2 and 3). The proteolytic fragment of IGF-BP-1 detected in 1-D gels (low molecular weight range, FIG. 5), Western blots (FIG. 6), and MS/MS analysis (FIG. 13) of trypsin digested ~10.5–12 KDa band from infected amniotic fluid, is represented in the region of the underlined sequence (SEQ ID No.: 4).

Indeed, MS/MS analysis and sequence search results demonstrated that the parent ion 434.89 in the mass spectrum shown in FIG. 13 represents an IGF-BP-1 sequence (RSPGSPEIR), which is also shown in the FIG. 12 sequence map of the IGF-BP-1 proteolytic fragment. The parent ion 1082.97 represents S-100 calcium binding proteins (i.e., Calgranulins A and B), also independently identified by de novo sequencing of AF (Tables 2 and 3).

Figure 14:
FIG. 14. Mass spectrum for the 17.55–18.21 minute retention time peak shown in FIG. 13.

FIG. 14 shows mass spectrum for the 17.55–18.21 minute retention time peak shown in FIG. 13. It is apparent that the dominate peak appears at mass 434.9.

Figure 15:
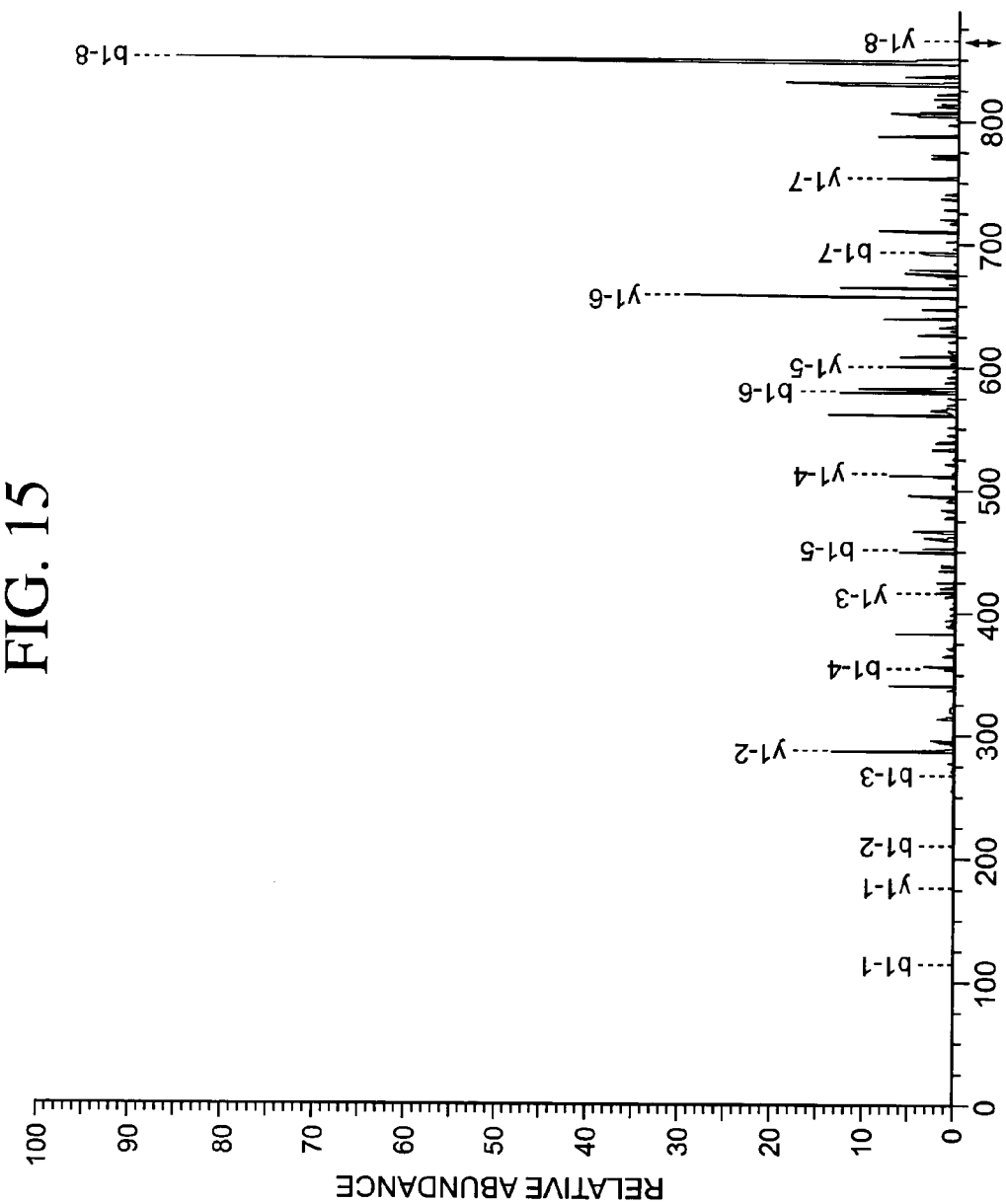
FIG. 15. MS/MS spectrum for the parent ion of the 434.9 peak shown in FIG. 14.

FIG. 15 shows the MS/MS spectrum for the parent ion of the 434.9 peak shown in FIG. 14. Based on database search, the parent ion corresponds to a partial sequence of IGFBP-1.

EXAMPLE 13

Diagnostic Profiles Characteristic of Chromosomal Aneuploidies

The utility of proteomic profiling was examined to identify trisomy-21 more accurately using maternal serum screening. This study was performed with a panel of (control (n=6), trisomy-21 (n=6) and trisomy-18 (n=4), well-characterized maternal serum samples (matching amniotic fluid samples for the same cases were tested by standard chromosomal mapping method and positively confirmed the presence of trisomies) and analyzed using SELDI-TOF methodology as described above for the intrauterine infection model.

Figure 10:
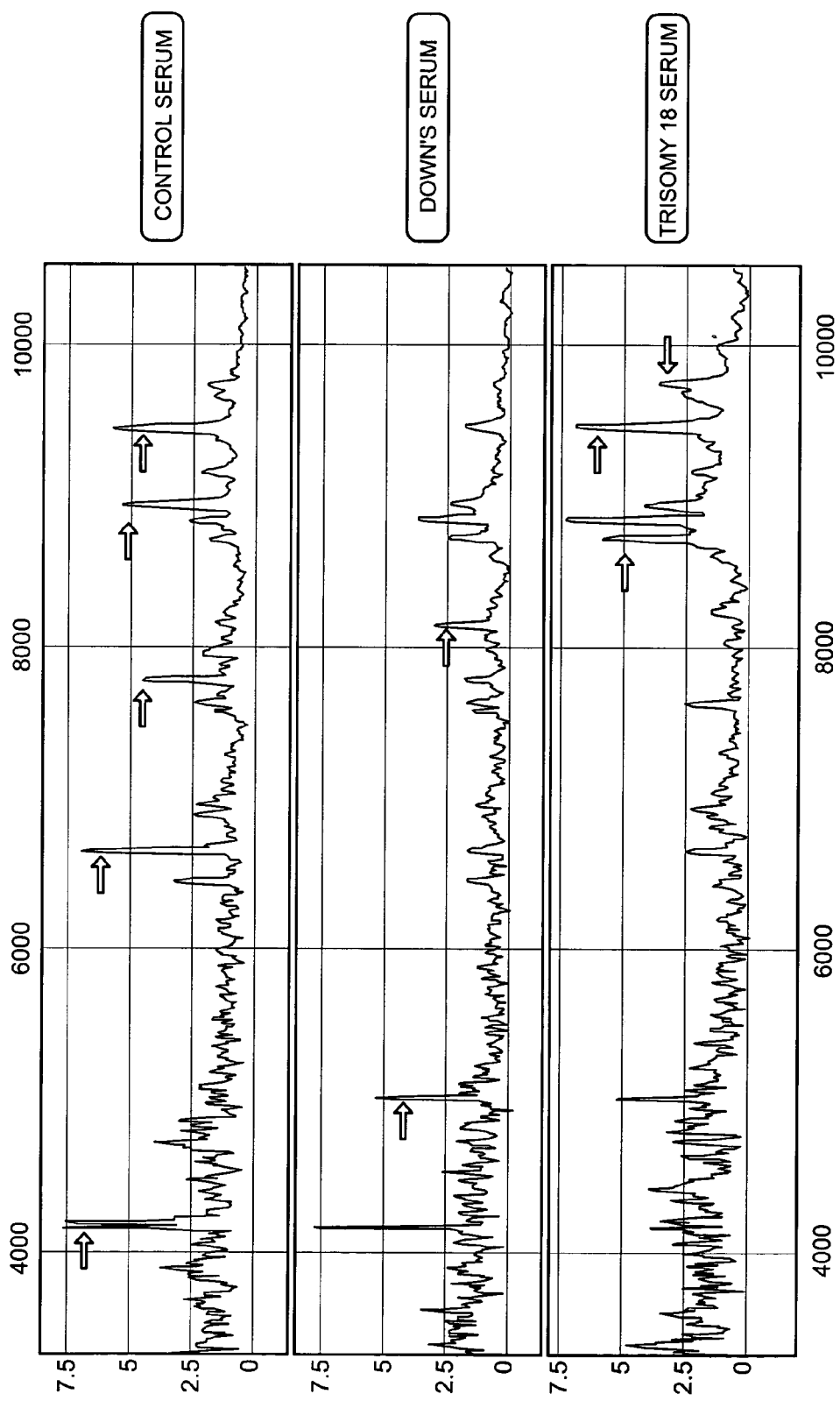
FIG. 10 shows differential protein expression patterns in the maternal serum with unique profiles to distinguish trisomies.

FIG. 10 shows differential protein expression patterns in the maternal serum with unique profiles to distinguish trisomies. One microgram of maternal serum (after removal of albumin and immunoglobulins using protein separation columns, BioRad technologies) was used to perform SELDI-TOF analysis of maternal serum extracts bound to chemically defined Normal Phase chip arrays as described in the methods. Whole spectrum collected at 235-laser intensity showing the differences in the peak intensities. A) Control serum; B) trisomy-21 (Down's) serum; C) trisomy-18 serum. Detailed spectrum showing the differences in the 4–15 KDa region unique for each case. Arrows indicate diagnostic peaks that can be used in a combination to formulate an algorithm to develop diagnostic screening tests.

This further illustrates detection of protein expression patterns in various biological fluids (such as maternal serum) could identify fetal-maternal conditions more accurately and in a non-invasive approach.

In conclusion, the data presented herein demonstrate that differential expression of proteins in the amniotic fluid as well as other biological fluids, such as serum, represents a valid approach for a rapid, non-invasive and accurate diagnosis, prognosis, and monitoring of various maternal/fetal conditions and chromosomal aneuploidies.

Throughout the foregoing description the invention has been discussed with reference to certain embodiments, but it is not so limited. Indeed, various modifications of the invention in addition to those shown and described herein will become apparent to those skilled in the art from the foregoing description and fall within the scope of the appended claims.

All references cited throughout the description, and the references cited therein, are hereby expressly incorporated by reference in their entirety.

What is claimed is:

1. A method for determining the state of a maternal condition selected from the group consisting of intra-uterine infection, intra-amniotic infection, and preterm labor, comprising:
   (a) comparing a proteomic profile of a test sample of a biological fluid selected from the group consisting of amniotic fluid, serum and plasma obtained from a mammalian subject with:
      (i) a proteomic profile of a normal sample, or
      (ii) a reference proteomic profile comprising at least one unique expression signature characteristic of said condition, wherein the test sample proteomic profile and the normal sample proteomic profile or the reference proteomic profile comprise information of the expression azurocidin, leukocyte elastase inhibitor, neutrophil gelatinase-associated lipocalin, and calgranulin B; or fragments or naturally occurring variants thereof that are functional in determining the state of the maternal condition, and wherein:
   (b) if the test proteomic profile is essentially the same as the normal sample proteomic profile the subject is determined to not possess the maternal condition, while if the test proteomic profile shows a unique expression signature relative to the normal sample proteomic profile the subject is determined to possess the maternal condition, or
   (c) if the test sample proteomic profile shares at least one unique expression signature characteristic with the reference sample the subject is determined to possess the maternal condition, while if the test sample proteomic profile does not share the at least one unique expression signature characteristic with the reference sample the subject is determined to not possess the maternal condition.

2. The method of claim 1 wherein said mammalian subject is a pregnant female.

3. The method of claim 2 wherein said pregnant female is human.

4. The method of claim 3 wherein said maternal condition is selected from the group consisting of intrauterine infection and preterm labor.

5. The method of claim 3 wherein said biological fluid is amniotic fluid or maternal serum.

6. The method of claim 1 wherein the proteomic profiles additionally comprise information of the expression of one or more of the following proteins: annexin II, L-plastin, macrophage capping protein, and cystatin; or fragments or naturally occurring variants thereof that are functional in determining the state of the maternal condition.

7. The method of claim 6 wherein the proteomic profiles additionally comprise information of the expression of one or more of the following proteins: mycloperoxidase, antibacterial protein FALL-39, Gp340 variant protein; Ebner salivary gland protein homolog (GENBANK™ Accession No AL355392) (SEQ ID NO: 12), calgranulin A, cofilin, moesin, profiling I, squamous cell carcinoma antigen 1, squamous cell carcinoma antigen 2, serpin 12, IGFBP-1, vitamin D-binding protein, apolipoprotein A-I, 14-3-3 protein sigma, 14-3-3 protein zeta/delta, gelsolin, lactotransferrin, phosphoglycerate kinase 1, phosphoglyceate mutase 1, and transketolase; or fragments or naturally occurring variants thereof that are functional in determining the state of the maternal condition.

8. The method of claim 7 wherein said proteomic profiles comprise information of the expression of at least 10 proteins.

9. The method of claim 7 wherein said proteomic profiles comprise information of the expression of at least 20 proteins.

10. The method of claim 7 wherein said proteomic profiles comprise information of the expression of at least 50 proteins.

11. The method of claim 7 wherein the proteomic profiles comprise information of the expression of all of said proteins, or fragments or naturally occurring variants thereof that are functional in determining the state of the maternal condition.

12. The method of claim 1 wherein the proteomic profiles are produced by mass spectrum analysis.

13. The method of claim 12 wherein the proteomic profile comprises at least one unique expression signature in the 3 to 5 kDa range of the mass spectrum.

14. The method of claim 12 wherein the proteomic profile comprises at least one unique expression signature in the 10 to 12 kDa range of the mass spectrum.

15. The method of claim 12 wherein the maternal condition is intra-amniotic infection, and the unique expression signature is an extra peak in the 10 to 11 kDa molecular weight range in the test sample, which is indicative of intra-amniotic infection.

16. The method of claim 15 wherein the biological fluid is amniotic fluid.

17. The method of claim 15 wherein the biological fluid is maternal serum.

18. The method of claim 1 wherein the proteomic profiles are produced by Western blot analysis.

19. The method of claim 1, wherein if the test proteomic profile is essentially the same as the normal sample proteomic profile the subject is determined to not possess of the maternal condition, while if the test proteomic profile shows a unique expression signature relative to said normal sample proteomic profile, the subject is determined to possess the maternal condition.

20. The method of claim 19 wherein the proteomic profiles additionally comprise information of the expression of one or more of the proteins selected from the group consisting of macrophage capping protein; myeloperoxidase; L-plastin; antibacterial protein FALL-39; calgranulin A; profilin I, glia-derived nexin; serpin 12; cystatin A; and IGFBP-1; or a fragment or naturally occurring variant thereof that are functional in determining the state of the maternal condition.

21. The method of claim 20 wherein the proteomic profiles comprise information of the expression of two or more of said proteins.

22. The method of claim 20 wherein the proteomic profiles comprise information of the expression of all of said proteins.

23. The method of claim 20 wherein the biological fluid is amniotic fluid.

24. The method of claim 23 wherein one or more of said proteins are differentially expressed in said test sample proteomic profile relative to said normal sample proteomic profile.

25. The method of claim 24 wherein said subject is diagnosed with intra-aniniotic infection.

26. The method of claim 23 wherein the test sample proteomic profile is essentially the same as the normal sample proteomic profile, and the subject is determined to be free of said maternal condition.

27. The method of claim 1 wherein the test sample proteomic profile contains the same unique expression signature as the reference sample proteomic profile.

28. The method of claim 27 wherein the unique expression signature is characteristic of intra-amniotic infection.

29. The method of claim 28 wherein said subject is diagnosed with intra-amniotic infection.

30. A method for the diagnosis of intra-amniotic infection, comprising
(a) comparing the proteomic profile of a test sample of a biological fluid selected from the group consisting of amniotic fluid, serum and plasma obtained from a pregnant female mammal with the proteomic profile of a normal sample, or a reference proteomic profile comprising at least one unique expression signature characteristic of said condition, wherein said proteomic profiles provide information of the mass of the proteins present in said samples, or the proteolytic fragments thereof;
(b) diagnosing said mammal with intra-aniniotic infection if the proteomic profile of the test sample shows a unique expression signature in the 3-5 and/or 10-12 KDa molecular weight range; and (c) wherein said test sample proteomic profile and said normal sample proteomic profile or reference proteomic profile comprise information of the expression of azurocidin, fragments or naturally occurring variants thereof that are functional in the diagnosis of intra-amniotic infection.

31. The method of claim 30 wherein the proteomic profiles are represented in the form of mass spectra.

32. The method of claim 31 wherein said mammal is a primate.

33. The method of claim 31 wherein said mammal is human.

34. The method of claim 33 further comprising the step of monitoring the course of said intra-amniotic infection.

35. The method of claim 31 wherein said biological fluid is amniotic fluid or maternal serum.

36. The method of claim 35 wherein at least one of azurocidin, leukocyte elastase inhibitor, neutrophil gelatinase-associated lipocalin, and calgranulin B; or a fragment or naturally-occurring variant thereof that is functional in the diagnosis of intra-amniotic infection, is overexpressed in said test sample proteomic profile relative to said normal sample proteomic profile.

37. The method of claim 35 wherein the test sample proteomic profile and the normal sample proteomic profile comprise information of the expression of L-plastin, and wherein L-plastin is underexpressed in said test sample proteomic profile relative to said normal sample proteomic profile.

38. The method of claim 30 wherein the biological fluid is amniotic fluid or maternal serum.

39. A method for the diagnosis of intra-amniotic infection, comprising:
(a) comparing the proteomic profile of a test sample of a biological fluid obtained from a pregnant female mammal with the proteomic profile of a normal sample wherein said test sample proteomic profile and said normal sample proteomic profile comprise information of the expression of azurocidin, leukocyte elastase inhibitor, neutrophil gelatinase-associated lipocalin, and calgranulin B; or fragments or naturally occurring variants thereof that are functional in diagnosis of the intra-amniotic infection, and
(b) diagnosing said mammal with intra-aniniotic infection if at least one protein selected from the group consisting of azurocidin, leukocyte elastase inhibitor, neutrophil gelatinase-associated lipocalin, and calgranulin B; or a fragment or naturally occurring variant thereof that is functional in the diagnosis of intra-aniniotic infection, is differentially expressed in said test sample relative to said normal sample.

40. The method of claim 39 wherein said mammal is a primate.

41. The method of claim 40 wherein said primate is human.

42. The method of claim 39 wherein the test sample proteomic profile and the normal sample proteomic profile comprise information of the expression of IGFBP-1, and the expression of IGFBP-1 is detected by identifying SEQ ID NO: 1, or a fragment thereof that is functional in the diagnosis of intra-amniotic infection.

43. The method of claim 39 further comprising the step of monitoring the state of said intra-aniniotic infection.

44. A method for the diagnosis of a maternal infection, comprising:
(a) comparing the proteomic profile of a test sample of a biological fluid obtained from a pregnant female mammal with the proteomic profile of a normal sample, or a reference proteomic profile comprising at least one unique expression signature characteristic of the infection;

(b) wherein said test sample proteomic profile and said normal sample proteomic profile or reference proteomic profile comprise information of the expression of azurocidin, leukocyte elastase inhibitor, neutrophil gelatinase-associated lipocalin, and calgranulin B; or fragments or naturally occurring variants thereof that are functional in the diaanosis of the maternal infection, and (c) confirming the presence of said maternal infection, if at least one protein, or a fragment thereof or a naturally occurring variant thereof that is functional in the diagnosis of the maternal infection, selected from the group consisting of azurocidin, leukocyte elastase inhibitor, neutrophil gelatinase-associated lipcalcin, and caigranulin B is;

(i) differentially expressed in said test sample proteomic profile relative to said normal sample proteomic profile, or (ii) expressed essentially the same in said test sample proteomic profile relative to said reference proteomic profile.

* * * * *

UNITED STATES PATENT AND TRADEMARK OFFICE
CERTIFICATE OF CORRECTION

PATENT NO. : 7,191,068 B2
APPLICATION NO. : 10/400005
DATED : March 13, 2007
INVENTOR(S) : Ron Rosenfield et al.

It is certified that error appears in the above-identified patent and that said Letters Patent is hereby corrected as shown below:

Column 39, Claims 25 and 30 should read as follows:

25. The method of claim 24 wherein said subject is diagnosed with intra-amniotic infection.

30. A method for the diagnosis of intra-amniotic infection, comprising (a) comparing the proteomic profile of a test sample of a biological fluid obtained from a pregnant female mammal with the proteomic profile of a normal sample, or a reference proteomic profile comprising at least one unique expression signature characteristic of said condition, wherein said proteomic profiles provide information of the mass of the proteins present in said samples, or the proteolytic fragments thereof;

(b) diagnosing said mammal with intra-amniotic infection if the proteomic profile of the test sample shows a unique expression signature in the 3-5 and/or 10-12 KDa molecular weight range; and (c) wherein said test sample proteomic profile and said normal sample proteomic profile or reference proteomic profile comprise information of the expression of azurocidin, leukocyte elastase inhibitor, neutrophil gelatinase-associated lipocalin, and calgranulin B; or fragments or naturally occurring variants thereof.

Column 40, Claims 39 and 43 should read as follows:

39. A method for the diagnosis of intra-amniotic infection, comprising:

(a) comparing the proteomic profile of a test sample of a biological fluid obtained from a pregnant female mammal with the proteomic profile of a normal sample wherein said test sample proteomic profile and said normal sample proteomic profile comprise information of the expression of azurocidin, leukocyte elastase inhibitor, neutrophil gelatinase-associated lipocalin, and calgranulin B; or fragments or naturally occurring variants thereof that are functional in diagnosis of the intra-amniotic infection, and (b) diagnosing said mammal with intra-amniotic infection if at least one protein selected from the group consisting of azurocidin, leukocyte elastase inhibitor, neutrophil gelatinase-associated lipocalin, and calgranulin B; or a fragment or naturally occurring variant thereof that is functional in the diagnosis of intra-amniotic infection, is differentially expressed in said test sample relative to said normal sample.

43. The method of claim 39 further comprising the step of monitoring the state of said intra-amniotic infection.

Column 40, Claim 44 should read as follows:

44. A method for the diagnosis of a material infection, comprising:

(a) comparing the proteomic profile of a test sample of a biological fluid obtained from a pregnant female mammal with the proteomic profile of a normal sample, or a reference proteomic profile comprising at least one unique expression signature characteristic of the infection;

(b) wherein said test sample proteomic profile and said normal sample proteomic profile or reference proteomic profile comprise information of the expression of azurocidin, leukocyte elastase inhibitor, neutrophil gelatinase-associated lipocalin, and calgranulin B; or fragments or naturally occurring variants thereof that are functional in the [ diaanosis] diagnosis of the maternal infection, and (c) confirming the presence of said maternal infection, if at least one protein, or a fragment thereof or a naturally occurring variant thereof that is functional in the diagnosis of the maternal infection, selected from the group consisting of azurocidin, leukocyte elastase inhibitor, neutrophil gelatinase-associated lipcalcin, and calgranulin B is;

(i) differentially expressed in said test sample proteomic profile relative to said normal sample proteomic profile, or
(ii) expressed essentially the same in said test sample proteomic profile relative to said reference proteomic profile.

Signed and Sealed this

Twenty-sixth Day of January, 2010

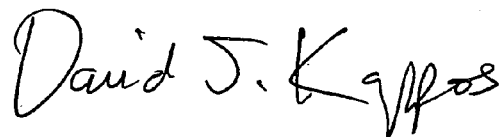

David J. Kappos
*Director of the United States Patent and Trademark Office*

UNITED STATES PATENT AND TRADEMARK OFFICE
CERTIFICATE OF CORRECTION

PATENT NO. : 7,191,068 B2
APPLICATION NO. : 10/400005
DATED : March 13, 2007
INVENTOR(S) : Ron Rosenfield et al.

It is certified that error appears in the above-identified patent and that said Letters Patent is hereby corrected as shown below:

Column 39, lines 39-40, Claim 25 should read as follows:

25. The method of claim 24 wherein said subject is diagnosed with intra-amniotic infection.

Column 39, line 52-Column 40, line 6, Claim 30 should read as follows:

30. A method for the diagnosis of intra-amniotic infection, comprising (a) comparing the proteomic profile of a test sample of a biological fluid obtained from a pregnant female mammal with the proteomic profile of a normal sample, or a reference proteomic profile comprising at least one unique expression signature characteristic of said condition, wherein said proteomic profiles provide information of the mass of the proteins present in said samples, or the proteolytic fragments thereof;

(b) diagnosing said mammal with intra-amniotic infection if the proteomic profile of the test sample shows a unique expression signature in the 3-5 and/or 10-12 KDa molecular weight range; and (c) wherein said test sample proteomic profile and said normal sample proteomic profile or reference proteomic profile comprise information of the expression of azurocidin, leukocyte elastase inhibitor, neutrophil gelatinase-associated lipocalin, and calgranulin B; or fragments or naturally occurring variants thereof.

Column 40, lines 32-51, Claim 39 should read as follows:

39. A method for the diagnosis of intra-amniotic infection, comprising:

(a) comparing the proteomic profile of a test sample of a biological fluid obtained from a pregnant female mammal with the proteomic profile of a normal sample wherein said test sample proteomic profile and said normal sample proteomic profile comprise information of the expression of azurocidin, leukocyte elastase inhibitor, neutrophil gelatinase-associated lipocalin, and calgranulin B; or fragments or naturally occurring variants thereof that are functional in diagnosis of the intra-amniotic infection, and (b) diagnosing said mammal with intra-amniotic infection if at least one protein selected from the group consisting of azurocidin, leukocyte elastase inhibitor, neutrophil gelatinase-associated lipocalin, and calgranulin B; or a fragment or naturally occurring variant thereof that is functional in the diagnosis of intra-amniotic infection, is differentially expressed in said test sample relative to said normal sample.

CERTIFICATE OF CORRECTION (continued)
U.S. Pat. No. 7,191,068 B2

Column 40, lines 62-63, Claim 43 should read as follows:

43. The method of claim 39 further comprising the step of monitoring the state of said intra-amniotic infection.

Column 40-Column 42, line 12, Claim 44 should read as follows:

44. A method for the diagnosis of a material infection, comprising:

(a) comparing the proteomic profile of a test sample of a biological fluid obtained from a pregnant female mammal with the proteomic profile of a normal sample, or a reference proteomic profile comprising at least one unique expression signature characteristic of the infection;

(b) wherein said test sample proteomic profile and said normal sample proteomic profile or reference proteomic profile comprise information of the expression of azurocidin, leukocyte elastase inhibitor, neutrophil gelatinase-associated lipocalin, and calgranulin B; or fragments or naturally occurring variants thereof that are functional in the [diaanosis] diagnosis of the maternal infection, and (c) confirming the presence of said maternal infection, if at least one protein, or a fragment thereof or a naturally occurring variant thereof that is functional in the diagnosis of the maternal infection, selected from the group consisting of azurocidin, leukocyte elastase inhibitor, neutrophil gelatinase-associated lipcalcin, and calgranulin B is;

(i) differentially expressed in said test sample proteomic profile relative to said normal sample proteomic profile, or
(ii) expressed essentially the same in said test sample proteomic profile relative to said reference proteomic profile.

This certificate supersedes the Certificate of Correction issued January 26, 2010.

Signed and Sealed this

Sixteenth Day of February, 2010

David J. Kappos
*Director of the United States Patent and Trademark Office*

SEQUENCE LISTING

<160> NUMBER OF SEQ ID NOS: 11

<210> SEQ ID NO 1
<211> LENGTH: 259
<212> TYPE: PRT
<213> ORGANISM: Homo sapiens

<400> SEQUENCE: 1

Met Ser Glu Val Pro Val Ala Arg Val Trp Leu Val Leu Leu Leu
1               5                   10                  15

Thr Val Gln Val Gly Val Thr Ala Gly Ala Pro Trp Gln Cys Ala Pro
            20                  25                  30

Cys Ser Ala Glu Lys Leu Ala Leu Cys Pro Pro Val Ser Ala Ser Cys
        35                  40                  45

Ser Glu Val Thr Arg Ser Ala Gly Cys Gly Cys Pro Met Cys Ala
    50                  55                  60

Leu Pro Leu Gly Ala Ala Cys Gly Val Ala Thr Ala Arg Cys Ala Arg
65                  70                  75                  80

Gly Leu Ser Cys Arg Ala Leu Pro Gly Glu Gln Gln Pro Leu His Ala
                85                  90                  95

-continued

```
Leu Thr Arg Gly Gln Gly Ala Cys Val Gln Glu Ser Asp Ala Ser Ala
            100                 105                 110

Pro His Ala Ala Glu Ala Gly Ser Pro Glu Ser Pro Glu Ser Thr Glu
        115                 120                 125

Ile Thr Glu Glu Leu Leu Asp Asn Phe His Leu Met Ala Pro Ser
    130                 135                 140

Glu Glu Asp His Ser Ile Leu Trp Asp Ala Ile Ser Thr Tyr Asp Gly
145                 150                 155                 160

Ser Lys Ala Leu His Val Thr Asn Ile Lys Lys Trp Lys Glu Pro Cys
                165                 170                 175

Arg Ile Glu Leu Tyr Arg Val Val Glu Ser Leu Ala Lys Ala Gln Glu
                180                 185                 190

Thr Ser Gly Glu Glu Ile Ser Lys Phe Tyr Leu Pro Asn Cys Asn Lys
            195                 200                 205

Asn Gly Phe Tyr His Ser Arg Gln Cys Glu Thr Ser Met Asp Gly Glu
        210                 215                 220

Ala Gly Leu Cys Trp Cys Val Tyr Pro Trp Asn Gly Lys Arg Ile Pro
225                 230                 235                 240

Gly Ser Pro Glu Ile Arg Gly Asp Pro Asn Cys Gln Ile Tyr Phe Asn
                245                 250                 255

Val Gln Asn

<210> SEQ ID NO 2
<211> LENGTH: 14
<212> TYPE: PRT
<213> ORGANISM: Homo sapien

<400> SEQUENCE: 2

Ala Leu Pro Gly Glu Gln Gln Pro Leu His Ala Leu Thr Arg
1               5                   10

<210> SEQ ID NO 3
<211> LENGTH: 9
<212> TYPE: PRT
<213> ORGANISM: Homo sapiens

<400> SEQUENCE: 3

Arg Ile Pro Gly Ser Pro Glu Ile Arg
1               5

<210> SEQ ID NO 4
<211> LENGTH: 94
<212> TYPE: PRT
<213> ORGANISM: Homo sapiens

<400> SEQUENCE: 4

Ala Leu His Val Thr Asn Ile Lys Lys Trp Lys Glu Pro Cys Arg Ile
1               5                   10                  15

Glu Leu Tyr Arg Val Val Glu Ser Leu Ala Lys Ala Gln Glu Thr Ser
                20                  25                  30

Gly Glu Glu Ile Ser Lys Phe Tyr Leu Pro Asn Cys Asn Lys Asn Gly
            35                  40                  45

Phe Tyr His Ser Arg Gln Cys Glu Thr Ser Met Asp Gly Glu Ala Gly
    50                  55                  60

Leu Cys Trp Cys Val Tyr Pro Trp Asn Gly Lys Arg Ile Pro Gly Ser
65                  70                  75                  80

Pro Glu Ile Arg Gly Asp Pro Asn Cys Gln Ile Tyr Phe Asn
                85                  90
```

```
<210> SEQ ID NO 5
<211> LENGTH: 139
<212> TYPE: PRT
<213> ORGANISM: Homo sapiens

<400> SEQUENCE: 5

Ala Gly Trp Asn Ala Tyr Ile Asp Asn Leu Met Ala Asp Gly Thr Cys
 1               5                  10                  15

Gln Asp Ala Ala Ile Val Gly Tyr Lys Asp Ser Pro Ser Val Trp Ala
            20                  25                  30

Ala Val Pro Gly Lys Thr Phe Val Asn Ile Thr Pro Ala Glu Val Gly
        35                  40                  45

Val Leu Val Gly Lys Asp Arg Ser Ser Phe Tyr Val Asn Gly Leu Thr
50                  55                  60

Leu Gly Gly Gln Lys Cys Ser Val Ile Arg Asp Ser Leu Leu Gln Asp
65                  70                  75                  80

Gly Glu Phe Ser Met Asp Leu Arg Thr Lys Ser Thr Gly Ala Pro
                85                  90                  95

Thr Phe Asn Val Thr Val Thr Lys Thr Asp Lys Thr Leu Val Leu Leu
            100                 105                 110

Met Gly Lys Glu Gly Val His Gly Leu Ile Asn Lys Lys Cys Tyr
        115                 120                 125

Glu Met Ala Ser His Leu Arg Arg Ser Gln Tyr
    130                 135

<210> SEQ ID NO 6
<211> LENGTH: 10
<212> TYPE: PRT
<213> ORGANISM: Homo sapiens

<400> SEQUENCE: 6

Pro Ser Val Trp Ala Ala Gly Pro Arg
 1               5                  10

<210> SEQ ID NO 7
<211> LENGTH: 14
<212> TYPE: PRT
<213> ORGANISM: Homo sapiens

<400> SEQUENCE: 7

Ser Thr Gly Gly Ala Pro Thr Phe Asn Val Thr Val Thr Lys
 1               5                  10

<210> SEQ ID NO 8
<211> LENGTH: 16
<212> TYPE: PRT
<213> ORGANISM: Homo sapiens

<400> SEQUENCE: 8

Thr Phe Val Asn Ile Thr Pro Ala Glu Val Gly Val Leu Val Gly Lys
 1               5                  10                  15

<210> SEQ ID NO 9
<211> LENGTH: 12
<212> TYPE: PRT
<213> ORGANISM: Homo sapiens

<400> SEQUENCE: 9

Asp Ser Pro Ser Val Trp Ala Ala Val Pro Gly Lys
 1               5                  10
```

```
<210> SEQ ID NO 10
<211> LENGTH: 12
<212> TYPE: PRT
<213> ORGANISM: Homo sapiens

<400> SEQUENCE: 10

Asp Ser Pro Ser Val Trp Ala Ala Val Pro Gly Lys
1               5                   10

<210> SEQ ID NO 11
<211> LENGTH: 16
<212> TYPE: PRT
<213> ORGANISM: Homo sapeins

<400> SEQUENCE: 11

Thr Phe Val Asn Ile Thr Pro Ala Glu Val Gly Val Leu Val Gly Lys
1               5                   10                  15
```